United States Patent
Eggler et al.

(10) Patent No.: US 12,201,649 B2
(45) Date of Patent: Jan. 21, 2025

(54) PHARMACEUTICAL COMPOSITION COMPRISING OXIDIZABLE BIPHENOL AND MANGANESE PORPHYRIN, AND METHOD OF USING THE SAME

(71) Applicant: Villanova University, Villanova, PA (US)

(72) Inventors: Aimee Eggler, Penn Valley, PA (US); Sandra Tamarin, Wynnewood, PA (US); Laura Biesterveld, Appleton, WI (US); Joseph LaMorte, Yardley, PA (US)

(73) Assignee: VILLANOVA UNIVERSITY, Villanova, PA (US)

( * ) Notice: Subject to any disclaimer, the term of this patent is extended or adjusted under 35 U.S.C. 154(b) by 13 days.

(21) Appl. No.: 17/985,504

(22) Filed: Nov. 11, 2022

(65) Prior Publication Data

US 2023/0149451 A1    May 18, 2023

Related U.S. Application Data

(60) Provisional application No. 63/278,604, filed on Nov. 12, 2021.

(51) Int. Cl.
*A61K 33/32* (2006.01)
*A61K 31/122* (2006.01)

(52) U.S. Cl.
CPC .......... *A61K 33/32* (2013.01); *A61K 31/122* (2013.01)

(58) Field of Classification Search
CPC ....... A61K 33/32; A61K 31/122; A61K 31/05
See application file for complete search history.

(56) References Cited

U.S. PATENT DOCUMENTS

| | | | |
|---|---|---|---|
| 8,546,562 B2 | 10/2013 | Crapo et al. | |
| 8,618,089 B2 | 12/2013 | Batinic-Haberle et al. | |
| 8,765,729 B2 | 7/2014 | Crapo et al. | |
| 8,946,202 B2 | 2/2015 | Crapo et al. | |
| 9,034,596 B1 | 5/2015 | Benov et al. | |
| 9,289,434 B2 | 3/2016 | Crapo et al. | |
| 10,080,759 B2 | 9/2018 | Ji et al. | |
| 11,065,259 B2 | 7/2021 | Ji et al. | |

OTHER PUBLICATIONS

Bauman et al. (Free Radical Biology and Medicine 124:532-540, 2018).*
Batinic-Haberle et al. (Antioxidants & Redox Signaling, 29 (16): 1691-1724, 2018).*
Okubo (Food and Chemical Toxicology 41: 679-688. 2003).*
American Cancer Society, Lifetime Risk of Developing or Dying From Cancer, https://www.cancer.org/healthy/cancer-causes/general-info/lifetime-probability-of-developing-or-dying-from-cancer.html, accessed Feb. 15, 2023, pp. 1-5.
Batinic-Haberle et al., Thiol regulation by Mn porphyrins, commonly known as SOD mimics, Redox Biology 25 (2019) 101139, pp. 1-14, https://doi.org/10.1016/j.redox.2019.101139.
Batinic-Haberle et al., H2O2-Driven Anticancer Activity of Mn Porphyrins and the Underlying Molecular Pathways, Hindawi, Oxidative Medicine and Cellular Longevity, vol. 2021, Article 1D6653790, 23 pages, https://doi.org/ I 0.11 55/2021 /6653790.
Polireddy et al., High Dose Parenteral Ascorbate Inhibited Pancreatic Cancer Growth and Metastasis: Mechanisms and a Phase I/IIa study, Scientific Reports, Dec. 7, 2017, pp. 1-15, Scientific Reports I 7: 17188 I DOI: 10.1038/s41598-017-17568-8.
Tovmasyan et al., Anticancer therapeutic potential of Mn porphyrin/ascorbate system, Free Radical Biology and Medicine, Oct. 2015, vol. 89, pp. 1231-1247, http://dx.doi.org/ 10.1016/j.freeradbiomed.2015.10.416.

* cited by examiner

*Primary Examiner* — Bong-Sook Baek
(74) *Attorney, Agent, or Firm* — DUANE MORRIS LLP

(57) ABSTRACT

A pharmaceutical composition and a method of using the same for killing cancer cells are provided. The pharmaceutical composition comprising effective amounts of one oxidizable diphenol and a manganese porphyrin in one-part dosage form or in a two-part dosage form. The oxidizable diphenol and the manganese porphyrin can be administrated to a subject in need thereof simultaneously or sequentially.

18 Claims, 24 Drawing Sheets

PHARMACEUTICAL COMPOSITION COMPRISING OXIDIZABLE BIPHENOL AND MANGANESE PORPHYRIN, AND METHOD OF USING THE SAME

PRIORITY CLAIM AND CROSS-REFERENCE

This application claims the benefit of U.S. Provisional Application No. 63/278,604, filed Nov. 12, 2021, which application is expressly incorporated by reference herein in its entirety.

FIELD OF THE INVENTION

The disclosure relates to pharmaceutical compositions and methods generally. More particularly, the disclosed subject matter relates to a pharmaceutical composition, a system, and a method for targeted cancer drug therapies.

BACKGROUND

In the U.S., one in five people will die from cancer. Most current cancer treatments including radiation and chemotherapies are toxic to both normal and cancer cells; more selective treatments could reduce side effects. In general, cancer cells are much more susceptible to oxidative and electrophilic stress than normal cells. This has been exploited in several existing therapies in clinical trials, including for ascorbic acid and manganese porphyrins, both of which cause oxidative stress in cancer cells. Moreover, the combination of ascorbic acid and a manganese porphyrin has been shown to be much more toxic to cancer cells than individual treatment using each ingredient, and non-toxic to normal cells.

SUMMARY

The present disclosure provides a pharmaceutical composition comprising one oxidizable diphenol and a manganese porphyrin, a system comprising the same, a method for making the pharmaceutical composition, and a method for using the same for targeted cancer drug therapies.

In one aspect, the present disclosure provides a pharmaceutical composition for killing cancer cells. Such a pharmaceutical composition comprises a pharmaceutically effective amount of an oxidizable diphenol and a pharmaceutically effective amount of a manganese porphyrin.

The manganese porphyrin is manganese (III) substituted pyridyl porphyrin in some embodiments. For example, the manganese porphyrin may be manganese (III) tetrakis (N-alkyl pyridyl) porphyrin, manganese (III) tetrakis (N-alkoxyl pyridyl) porphyrin, or any combination thereof. The pyridyl is 2-pyridyl, 3-pyridyl, 4-pyridyl, or any combination thereof. The alkyl or alkoxyl is optionally further substituted. The manganese porphyrin may be selected from manganese (III) tetrakis (N-alkyl 2-pyridyl) porphyrin, manganese (III) tetrakis (N-alkyl 3-pyridyl) porphyrin, manganese (III) tetrakis (N-alkyl 4-pyridyl) porphyrin, manganese (III) tetrakis (N-alkoxyl 2-pyridyl) porphyrin, manganese (III) tetrakis (N-alkoxyl 3-pyridyl) porphyrin, manganese (III) tetrakis (N-alkoxyl 4-pyridyl) porphyrin, and any substituted derivative thereof or any combination thereof.

The oxidizable diphenol may be a diphenol as defined and described herein. For example, the oxidizable diphenol may be 1, 2-diphenol, 1, 4-diphenol, 1, 6-diphenol, and any substituted compound or derivative thereof. In some embodiments, the oxidizable diphenol is hydroquinone or a substituted hydroquinone.

The pharmaceutical composition may also comprise a pharmaceutically acceptable carrier or excipient.

The oxidizable diphenol and the manganese porphyrin as described herein can be combined in one composition, or are in two parts of composition for sequential administration. For example, in some embodiments, the oxidizable diphenol and the manganese porphyrin can be administrated subcutaneously. They may be solution dosages for sequential administration. For example, in some embodiments, the oxidizable diphenol and the manganese porphyrin can be combined in one dosage form such as a tablet for oral administration. In some embodiments, the oxidizable diphenol and the manganese porphyrin are two separate parts, which can be in solid or solution dosages, and sequentially and orally administered into a subject in need thereof. In some embodiments, more than one oxidizable diphenol can be used, in combination with one or more than one manganese porphyrin compounds.

In some embodiments, the oxidizable diphenol and the manganese porphyrin are at a molar ratio in a range of from about 1:3 to about 5:1, for example, from about 1:2 to about 5:3.

The pharmaceutical composition in one-part or two-part can be administrated to a subject in need thereof for treating a cancer targeting to kill cancer cells. The cancer may be pancreatic cancer, acute T cell leukemia, acute lymphoblastic leukemia, breast cancer, prostate cancer, or any other cancer type.

In one aspect, the present disclosure provides a method for treating or curing a cancer. The method is provided for treating, curing, providing symptomatic relief, reducing the severity of, or reducing complications of a cancer. Such a method comprises administrating a pharmaceutically effective amount of an oxidizable diphenol and a pharmaceutically effect amount of manganese porphyrin as described herein to a subject in need thereof so as to kill cancer cells.

The oxidizable diphenol and the manganese porphyrin can be administrated simultaneously in one step in a pharmaceutical composition comprising both ingredients, or administrated separately in a two-part composition. The term "effective amount" as used herein means an amount of a composition or an ingredient sufficient to kill at least some cancer cells so as to treat, cure, or lessen the severity of a cancer. The ingredients or the composition can be administrated alone or as an adjuvant in combination with chemotherapeutics such as gemcitabine.

In another aspect, the present disclosure also provides a system comprising such a composition or the ingredients as described, using the method as described for targeted cancer drug therapies.

BRIEF DESCRIPTION OF THE DRAWINGS

The present disclosure is best understood from the following detailed description when read in conjunction with the accompanying drawings. It is emphasized that, according to common practice, the various features of the drawings are not necessarily to scale. On the contrary, the dimensions of the various features are arbitrarily expanded or reduced for clarity. Like reference numerals denote like features throughout specification and drawings.

DETAILED DESCRIPTION

Figure 1:
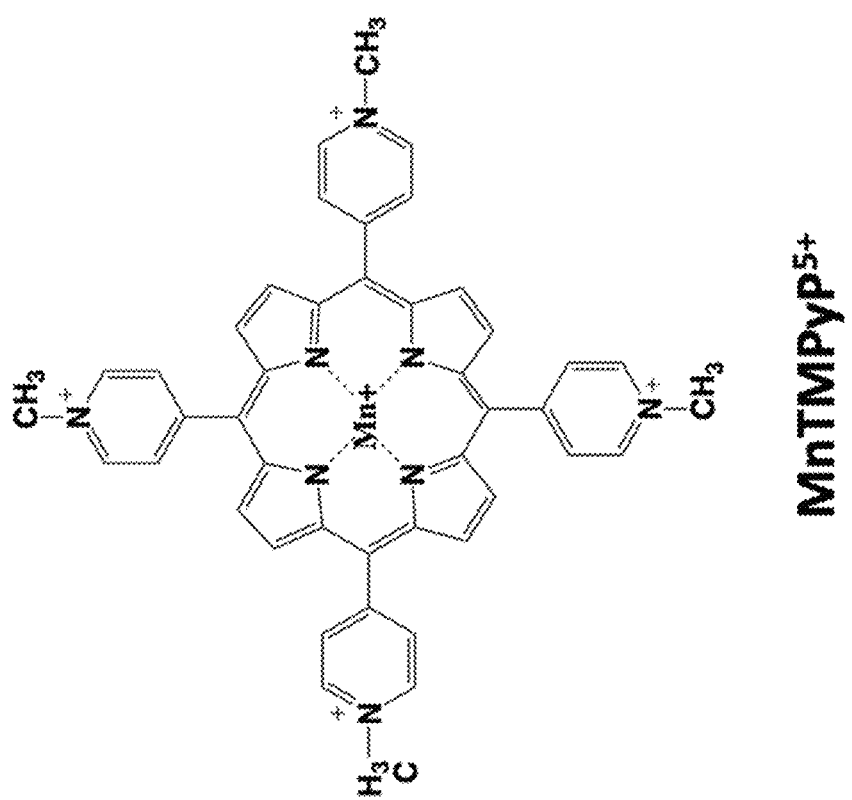
FIG. 1 shows structure of an exemplary manganese porphyrin, Mn(III)tetrakis(1-methyl-4-pyridyl)porphyrin (MnTMPyP).

This description of the exemplary embodiments is intended to be read in connection with the accompanying drawings, which are to be considered part of the entire written description.

For purposes of the description hereinafter, it is to be understood that the embodiments described below may assume alternative variations and embodiments. It is also to be understood that the specific articles, compositions, and/or processes described herein are exemplary and should not be considered as limiting.

In the present disclosure the singular forms "a," "an," and "the" include the plural reference, and reference to a particular numerical value includes at least that particular value, unless the context clearly indicates otherwise. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive; as another example, the phrase "about 8%" preferably (but not always) refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

The problem to address is the need to target cancer cells for death, while preserving the health of non-cancer tissues. Most cancer therapeutics are generally toxic, thereby damaging healthy tissue while causing more toxicity to cancer cells. An approach to specifically target cancer cells is to take advantage of their higher susceptibility to oxidative and electrophilic stress than normal human cells. Oxidizable phenols, ascorbic acid, and manganese porphyrins all generate oxidative stress. Further, ascorbic acid, which like an oxidizable phenol can donate electrons to oxygen to produce reactive oxygen species, has been combined with manganese porphyrins in preclinical trials.

The present disclosure provides a method and a composition for treating, curing, providing symptomatic relief, reducing the severity of, or reducing complications of, a cancer.

The term "pharmaceutically effective amount" as used herein means an amount of a composition or an ingredient sufficient to kill cancer cells so as to treat, cure, or lessen the severity of a cancer, when administrated alone or as an adjuvant in combination with chemotherapeutics such as gemcitabine.

The term "subject" or "patient" as used herein refers to an animal, preferably a mammal, most preferably a human, who has been the object of treatment, observation or experiment.

The term "alkyl" as used herein refers to a straight chain, cyclic, branched or unbranched saturated or unsaturated hydrocarbon chain containing 1-10 carbon atoms, such as methyl, ethyl, propyl, tert-butyl, n-hexyl and the like. "A $C_{1-6}$ alkyl" as used herein refers to an alkyl group having a number of carbon atoms selected from 1 to 6.

The term "optionally substituted" means that group in question may be unsubstituted or it may be substituted one or several times, such as 1 to 3 times or 1 to 5 times. For example, an alkyl group that is "optionally substituted" with 1 to 5 chloro atoms, may be unsubstituted, or it may contain 1, 2, 3, 4, or 5 chlorine atoms. Substituted chemical moieties include one or more substituents that replace hydrogen.

The substituted derivatives are based on each of these two compounds, in which one or more substitution groups are bonded onto one or more ring structures. Examples of a suitable substitution group include, but are not limited to, fluoro, chloro, amino, carboxyl, alkyl, or other suitable groups or a combination thereof.

In the present disclosure, at least one oxidizable phenol is combined with at least one manganese porphyrin. This combination can be much more, for example, 1000 times more potent at killing cancer cells than ascorbic acid combined with the same manganese porphyrin, due to the electrophilic oxidized form of the phenol. The manganese porphyrin catalyzes the oxidation of the phenol.

The manganese porphyrin can be a manganese (III) substituted pyridyl porphyrin. The substitution group on the pyridyl ring may be N-substituted, and may be alkyl, alkoxyl, alkoxyalkyl, carboxyl, or any combination thereof. Porphyrin rings may be also substituted. In some embodiments, the manganese porphyrin is manganese (III) tetrakis (N-alkyl pyridyl) porphyrin, manganese (III) tetrakis (N-alkoxyl pyridyl) porphyrin, or any combination thereof. The alkyl group may be any C1-6 alkyl such as methyl, ethyl, propyl, isopropyl, butyl, iso-butyl, tert-butyl, pentyl, hexyl, or any combination thereof. The alkyl or alkoxyl group may be further substituted. Examples of a suitable substitution group include, but are not limited to, fluoro, chloro, amino, carboxyl, alkyl, or other suitable groups or a combination thereof. The pyridyl group can be 2-pyridyl, 3-pyridyl, 4-pyridyl or any combination thereof. The nitrogen in the pyridyl group may be in ortho (2), meta (3), or para (4) position. So examples of the manganese porphyrin may include, but not limited to, manganese (III) tetrakis (N-alkyl 2-pyridyl) porphyrin, manganese (III) tetrakis (N-alkyl 3-pyridyl) porphyrin, manganese (III) tetrakis (N-alkyl 4-pyridyl) porphyrin, manganese (III) tetrakis (N-alkoxyl 2-pyridyl) porphyrin, manganese (III) tetrakis (N-alkoxyl 3-pyridyl) porphyrin, manganese (III) tetrakis (N-alkoxyl 4-pyridyl) porphyrin, any substituted derivatives, or any combination thereof. In some embodiments, the manganese porphyrin is cationic with anions as counter ions. Examples of anions include, but are not limited to Cl⁻, $SO_4^{2-}$ and any other suitable anions. A manganese porphyrin compound may be abbreviated as "MnP" while its cationic form is presented in a form of "$MnP^{x+}$" or "MnPx+" such as MnP5+ when X=5. The forms "MnP" and "MnPx+" are used interchangeably in the present disclosure. For example, manganese (III) tetrakis(N-methyl-4-pyridyl)porphyrin (MnTMPyP) and its ionic form $MnTMPyP^{5+}$ are used interchangeably. In the ionic form, the counterions can be any suitable anions. For example, in the examples, the counter ions for $MnTMPyP^{5+}$ used in the present disclosure is Cl− and the manganese porphyrin compound is MnTMPyP pentachloride.

Examples of a suitable manganese porphyrin include, but are not limited to, manganese (III) tetrakis(N-methyl-4-pyridyl)porphyrin (MnTMPyP), manganese (III) meso-tetrakis(N-ethylpyridinium-2-yl)porphyrin (MNTE-2-PyP), manganese (III) meso-tetrakis(N-n-butoxyethyl-pyridinium-2-yl)porphyrin (MnTNBuOE-2-PyP), manganese (III) tetrakis(N-methyl-2-pyridyl)porphyrin (MnTM-2-PyP), manganese (III) tetrakis(N-methyl-3-pyridyl)porphyrin (MnTM-3-PyP), manganese (III) tetrakis(N-methyl-4-pyridyl)porphyrin (MnTM-4-PyP), manganese (III) tetrakis(N-ethyl-3-pyridyl)porphyrin (MnTE-3-PyP), manganese (III) tetrakis(N-ethyl-4-pyridyl)porphyrin (MnTE-4-PyP), manganese (III) tetrakis(N-propyl-2-pyridyl)porphyrin (MnPr-2-PyP), manganese (III) tetrakis(N-propyl pyridyl)porphyrin (MnPr-3-PyP), manganese (III) tetrakis(N-propyl-4-pyridyl)porphyrin (MnPr-4-PyP), manganese (III) tetrakis (N-butyl-2-pyridyl)porphyrin (MnBU-2-PyP), manganese (III) tetrakis(N-butyl-3-pyridyl)porphyrin (MnBU-3-PyP), manganese (III) tetrakis(N-butyl pyridyl)porphyrin (MnBU-4-PyP), manganese (III) tetrakis(N-pentyl-2-pyridyl)porphyrin (MnPen-2-PyP), manganese (III) tetrakis(N-pentyl-3-pyridyl)porphyrin (MnPen-3-PyP), manganese (III) tetrakis(N-pentyl-4-pyridyl)porphyrin (MnPen-4-PyP), manganese (III) tetrakis(N-hexyl-2-pyridyl)porphyrin (Mn-Hex-2-PyP), manganese (III) tetrakis(N-hexyl-3-pyridyl) porphyrin (MnHex-3-PyP), manganese (III) tetrakis(N-hexyl-4-pyridyl)porphyrin (MnHex-4-PyP), manganese (III) tetrakis(N-ethylpyridinium-3-yl)porphyrin (MNTE-3-PyP), manganese (III) tetrakis(N-n-butoxyethyl-pyridinium-4-yl)porphyrin (MnTNBuOE-4-PyP), manganese (III) tetrakis(N-ethylpyridinium-3-yl)porphyrin (MNTE-3-PyP), manganese (III) tetrakis(N-n-butoxyethyl-pyridinium-4-yl) porphyrin (MnTNBuOE-4-PyP), manganese (III) tetrakis (N-carboxyl-4-pyridyl)porphyrin (MnTBAP) and any combination thereof.

Some suitable manganese porphyrins are described in Artak Tovmasyan et al., "Anticancer therapeutic potential of Mn porphyrin/ascorbate system," *Free Radical Biology and Medicine,* 89(2015) 1231-1247, which is incorporated herein by reference, and can be used in the composition and the method provided in the present disclosure.

The term "oxidizable diphenol" can be understood to encompass a compound having a dihydroxybenzene moiety, in which two hydroxyl groups are substituted onto a benzene ring, and also encompass a compound having a bicyclic moiety including one benzene ring and one cyclic structure comprising carbon-carbon double bonds, while also having two hydroxyl groups. An oxidizable diphenol can be 1, 2-diphenol, 1, 4-diphenol, 1, 6-diphenol, and substituted compounds or derivatives thereof. For example, an oxidizable diphenol may include 1, 2-diphenol moiety, in which two hydroxyl groups in 1- and 2-positions of a phenyl ring. An oxidizable diphenol may include 1, 4-diphenol moiety, in which two hydroxyl groups in 1- and 4-positions of a phenyl ring. In some embodiments, an oxidizable diphenol may include a bicyclic structure including a phenyl ring and a ring structure having at least one C=C bond, and have one hydroxyl group on a phenyl ring (at 1-position), while having another hydroxyl group on the 6-position of the compound in the ring structure having C=C bond. The oxidizable diphenol is electrophilic.

In some embodiments, the oxidizable diphenol is a substituted hydroquinone as one example. The substitution group may be alkyl, alkoxyl, alkoxyalkyl, carboxyl, or any combination thereof. The alkyl group may be any $C_{1-6}$ alkyl such as methyl, ethyl, propyl, isopropyl, butyl, iso-butyl, tert-butyl, pentyl, hexyl, or any combination thereof. The alkyl or alkoxyl group may be further substituted. Examples of a suitable substitution group include, but are not limited to, fluoro, chloro, amino, carboxyl, alkyl, or other suitable groups or a combination thereof. In some embodiments, the oxidizable diphenol contains only one substitution group between the two hydroxyl groups (i.e., 1,4-diphenol) in the substituted hydroquinone.

Examples of a suitable oxidizable diphenol include, but are not limited to tert-butylhydroquinone (tBHQ), methylhydroquinone, ethylhydroquinone, n-propylhydroquinone, isopropylhydroquinone, n-butylhydroquinone, isobutylhydroquinone, or any combination thereof.

The pharmaceutical composition may also comprise a pharmaceutically acceptable carrier or excipient.

The oxidizable diphenol and the manganese porphyrin as described herein can be combined in one composition, or are in two parts of composition for sequential administration. For example, in some embodiments, the oxidizable diphenol and the manganese porphyrin can be administrated subcutaneously. For example, in some embodiments, the oxidizable diphenol and the manganese porphyrin can be combined in one-part dosage form such as a tablet for oral administration. In some embodiments, the oxidizable diphenol and the manganese porphyrin are two separate parts, which can be in solid or solution dosages, and sequentially and orally administered into a subject in need thereof. In some embodiments, more than one oxidizable diphenol can be used, in combination with one or more than one manganese porphyrin compounds.

In some embodiments, the oxidizable diphenol and the manganese porphyrin are at a molar ratio in a range of from about 1:3 to about 5:1, for example, from about 1:2 to about 5:3.

In another aspect, the present disclosure provides a method of making the pharmaceutical composition as described herein. Such a method may include steps of providing a pharmaceutically effective amount of an oxidizable diphenol, providing a pharmaceutically effective amount of a manganese porphyrin (MnP), and mixing the oxidizable diphenol and the manganese porphyrin. The method may also include one or more steps of mixing a pharmaceutically acceptable carrier or excipient with the oxidizable diphenol, the manganese porphyrin, or a combination of the oxidizable diphenol and the manganese porphyrin. The carrier or excipient may include a solvent. The composition may be made in a one or two-part formulation. For example, in the cell culture studies described in the present disclosure, the oxidizable diphenol such as tBHQ was dissolved in dimethyl sulfoxide (DMSO) to provide a 0.05% solution in the cell media, and the MnP was dissolved in water. The MnP compounds as described herein can be dissolved in water to provide an aqueous solution, and MnP becomes ionized.

The pharmaceutical compositions in one-part or two-part can be administrated to a subject in need thereof for treating a cancer targeting to kill cancer cells. The cancer may be pancreatic cancer, acute T cell leukemia, acute lymphoblastic leukemia, breast cancer, prostate cancer, or any other cancer type.

In one aspect, the present disclosure provides a method for treating or curing a cancer. The method is provided for treating, curing, providing symptomatic relief, reducing the severity of, or reducing complications of a cancer. Such a method comprises administrating a pharmaceutically effective amount of an oxidizable diphenol and a pharmaceutically effect amount of manganese porphyrin as described herein to a subject in need thereof so as to kill cancer cells.

The oxidizable diphenol and the manganese porphyrin can be administrated simultaneously in one step in a pharmaceutical composition comprising both ingredients, or administrated separately in a two-part composition. The term "effective amount" as used herein means an amount of a composition or an ingredient sufficient to kill at least some cancer cells so as to treat, cure, or lessen the severity of a cancer. The ingredients or the composition can be administrated alone or as an adjuvant in combination with chemotherapeutics such as gemcitabine.

In some embodiments, the MnP can be administered systemically, in the same fashion used for radiation co-treatment in the clinical trials, in order to have the demonstrated radio-protective effect, while the oxidizable diphenol such as tBHQ can be administered locally to the tumor environment where the systemic MnP would oxidize it to the quinone.

In another aspect, the present disclosure also provides a system comprising such a composition or the ingredients as described, using the method as described for targeted cancer drug therapies.

As one example of the manganese porphyrin in the present disclosure, Mn(III)tetrakis(1-methyl-4-pyridyl)porphyrin (MnTMPyP) as shown in FIG. 1 is used in some embodiments. MnTMPyP is commercially available. The MnTMPyP used in the examples described herein was purchased from Santa Cruz Biotechnology of Dallas, Texas (Catalog #SC-221956).

In the present disclosure, a pro-electrophilic oxidizable phenol is combined with a manganese porphyrin for treating to kill cancer cells. Examples of cancer cells include, but are not limited to, leukemic cancer cells, acute lymphoblastic leukemia NALM6 cells, MDA-MB-231 breast cancer cells, and PC3 prostate cancer cells.

Figure 2:
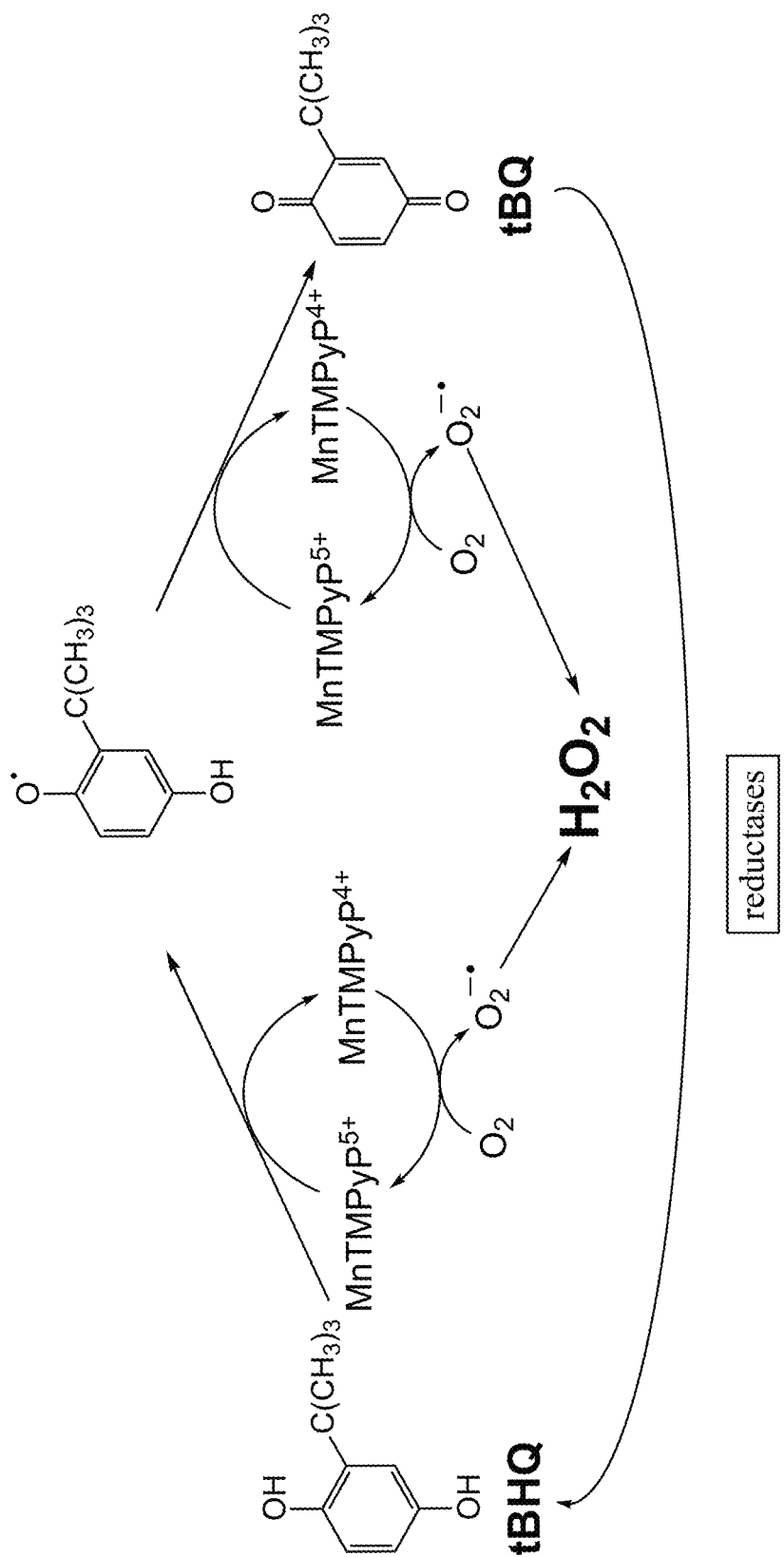
FIG. 2 is a schematic of a proposed chemical mechanism for an exemplary method and an exemplary composition provided in the present disclosure in accordance with some embodiments, while the present disclosure is not bound by any theory.

In some embodiments, a pro-electrophilic oxidizable phenol, for example, tert-butylhydroquinone (tBHQ), is combined with a manganese porphyrin, for example, MnTMPyP, in a treatment to kill cancer cells, for example, in acute T cell leukemia (Jurkat cells). FIG. 2 is a schematic of a proposed chemical mechanism for the method and the composition provided in the present disclosure in accordance with some embodiments, while the present disclosure is not bound by any theory. The chemical mechanism is shown in FIG. 2 using MnTMPyP as an example of manganese porphyrin (MnP) and tBHQ as one example of oxidizable phenol. The manganese porphyrin such as MnTMPyP progressively catalyzes the oxidation of the oxidizable phenol such as tBHQ, generating both the electrophilic quinone tBQ and reactive oxygen species (ROS). The reactive oxygen species as shown in FIG. 2 include superoxide and hydrogen peroxide. Both the quinone and hydrogen peroxide are toxic, in particular to cancer cells. During reaction, the valence of Mn decreases to oxidize the biphenol. The term "reductases" in FIG. 2 indicate cellular reductases. The cellular reductases are present in the intracellular environment and can create a cycle of tBHQ oxidation and reduction, which would in turn continue to generate more and more $H_2O_2$ and other reactive oxygen species. However, as the data described herein show, the $H_2O_2$ generated in this way does not contribute to cell death. Instead, the quinone generated contribute to cancer cell death.

The results described herein show that an oxidizable diphenol combined with a manganese porphyrin induces mitochondrial oxidative stress, apoptosis, and necrosis in cancer cells. Examples of the cancer cells include, but are not limited to, leukemic cancer cells, acute lymphoblastic leukemia NALM6 cells, MDA-MB-231 breast cancer cells, and PC3 prostate cancer cells.

The oxidation of phenol tert-butylhydroquinone (tBHQ) is catalyzed by MnTMPyP. While hydrogen peroxide can be generated, the electrophilic, oxidized form of tBHQ, tBQ is also formed. Quinones have known toxicity to cells, and quinones such as tBQ is likely the active agent that is cytotoxic to cancer cells.

Figure 3:
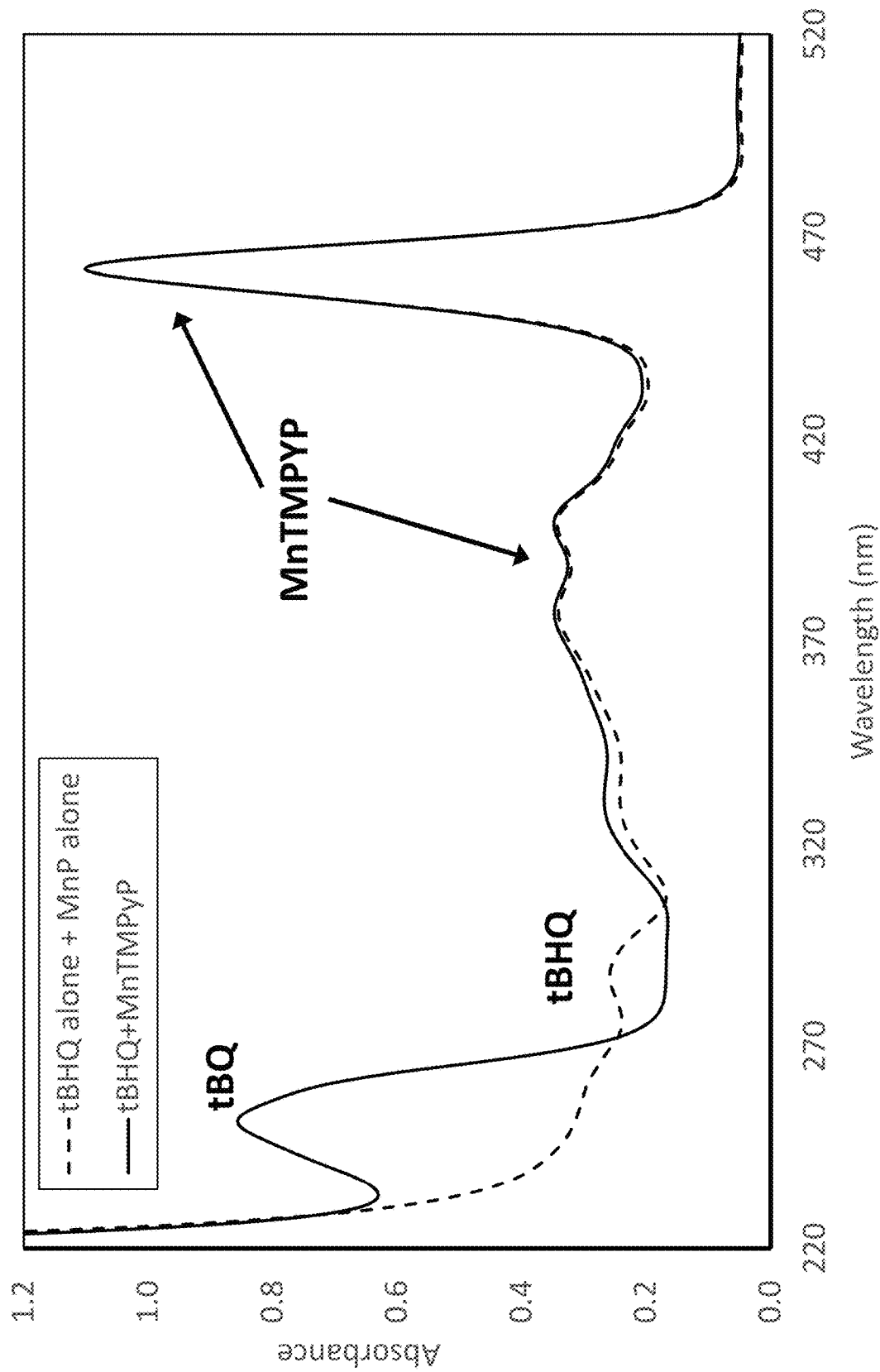
FIG. 3 shows ultra-violet/visible light spectroscopy results illustrating MnTMPyP catalyzes oxidation of tert-butyl hydroquinone (tBHQ) to tert-butyl quinone (tBQ).

Referring to FIG. 3, solutions were prepared in 100 μM phosphate buffer at pH 7.5. Such solutions were made in new plastic vials to avoid any risk of metal contamination. For the trace shown by a solid black line, 250 μM tBHQ was combined with 12 μM MnTMPyP, and for the trace shown by the dashed line, each was prepared separately. The absorbance of each was measured by ultra-violet/visible light spectroscopy. The results of ultra-violet/visible light spectroscopy at wavelengths in the range of from 220 nm to 520 nm are shown in FIG. 3. The black line shows the absorbance spectrum for the mixture of tBHQ and MnTMPyP, and the dashed line shows the combined (added) spectra for both.

As shown in FIG. 3, the results of ultra-violet/visible light spectroscopy show that MnTMPyP catalyzes oxidation of tert-butyl hydroquinone (tBHQ) to tert-butyl quinone (tBQ). Compared to the curve in the dotted line, in the in the mixture of tBHQ and MnTMPyP, the intensity of the peak at wavelength of from about 270 nm to about 300 nm corresponding to tBHQ significantly decreases. Meanwhile, the intensity of the peak at wavelength of from about 230 nm to about 270 nm corresponding to tBQ significantly increases. The spectrum of the manganese porphyrin, MnTMPyP, remains unchanged, as it acts catalytically.

Further studies of toxicity of a compound or a combination of compounds were performed according to the testing procedures as follows:

Referring to FIGS. 4, 5, 6, 8, 12 and 15, cells were treated with the indicated compounds or vehicle for 4 hours in RPMI medium with 10% fetal bovine serum (FBS). RPMI medium, also known as RPMI 1640, is a growth medium used in cell culture. In these and other figures, "vehicle" represents when a treatment compound is omitted and replaced with the vehicle that the compound is dissolved in. Thus, when a MnP is omitted, water is added in its place. When an oxidizable phenol is omitted, DMSO is added for a resulting final concentration in the cell media of 0.05% DMSO. Apoptosis was measured using Annexin-PE, and necrosis was measured with RedDot 2. Fluorescence was read on an Accuri C6 flow cytometer with excitation from a 488 nm laser, and FL2 and FL4 filters were used for Annexin-PE and RedDot2, respectively. 10,000 events were acquired. Flow cytometry data was analyzed using Flowlogic software from Inivai Technologies of Australia. Samples were gated using forward and side scatter to exclude debris, and quadrant analysis of FL2 versus FL4 was used to assign cells as alive (both dyes excluded), apoptotic (Annexin-PE positive but RedDot2 excluded), or necrotic (RedDot2 positive). Percentage of alive, apoptotic, or necrotic cells was determined and graphed as the average±the standard deviation.

Figure 9:
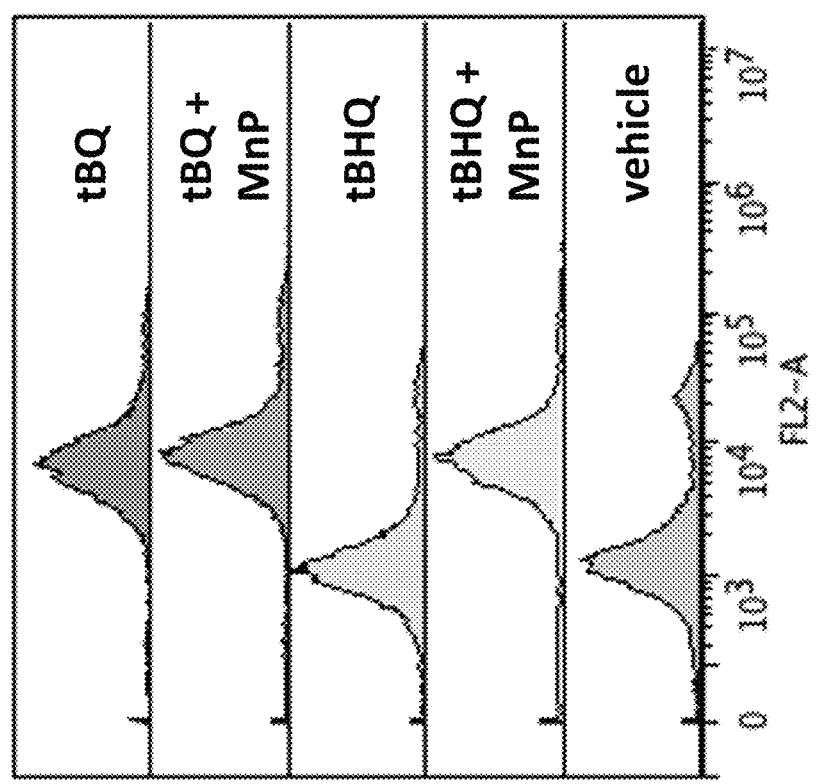
FIG. 9 shows that the quinone tBQ alone is sufficient to cause apoptosis in Jurkat cells. The results are unaffected by inclusion of MnTMPyP into tBQ.
Figure 13:
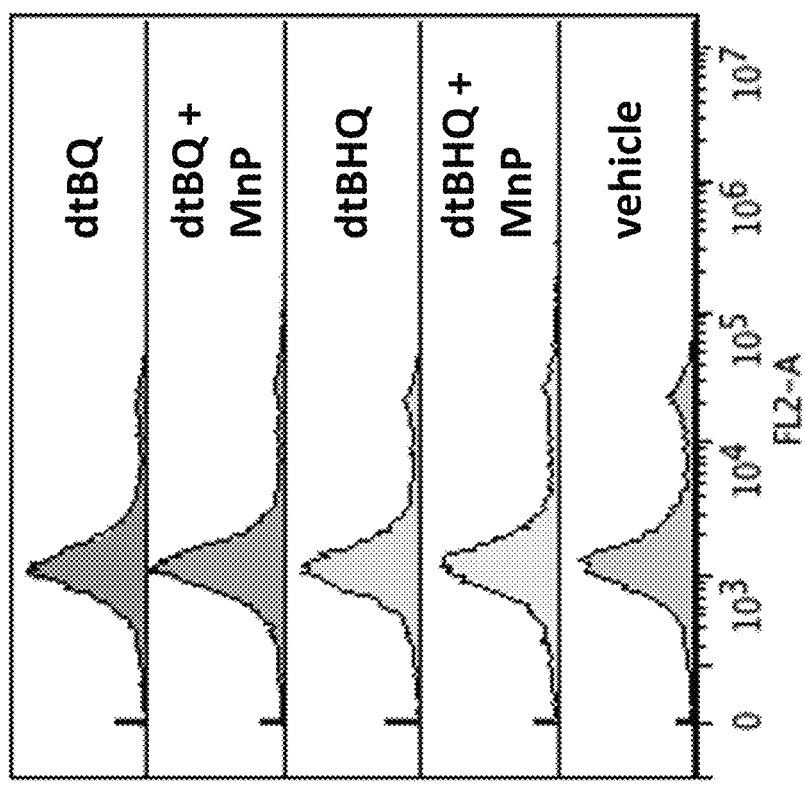
FIG. 13 are ultra-violet/visible light spectroscopy results showing that dtBHQ, dtBHQ in combination with MnTMPyP, and dtBQ all show no production of ROS in the mitochondria.

Referring to FIGS. 9 and 13, Jurkat cells were treated with the indicated compounds for 4 hours in RPMI with 10% FBS. Mitochondrial ROS were measured using the MitoSOX Red dye, which enters living cells, targets the mitochondria, and is preferentially oxidized by superoxide. Fluorescence was read on an Accuri C6 flow cytometer with excitation from a 488 nm laser and an FL2 filter. 10,000 events were acquired. Flow cytometry data was analyzed using Flowlogic software. Samples were gated using forward and side scatter to exclude debris, and the signal intensity versus number of events was plotted.

Figure 16:
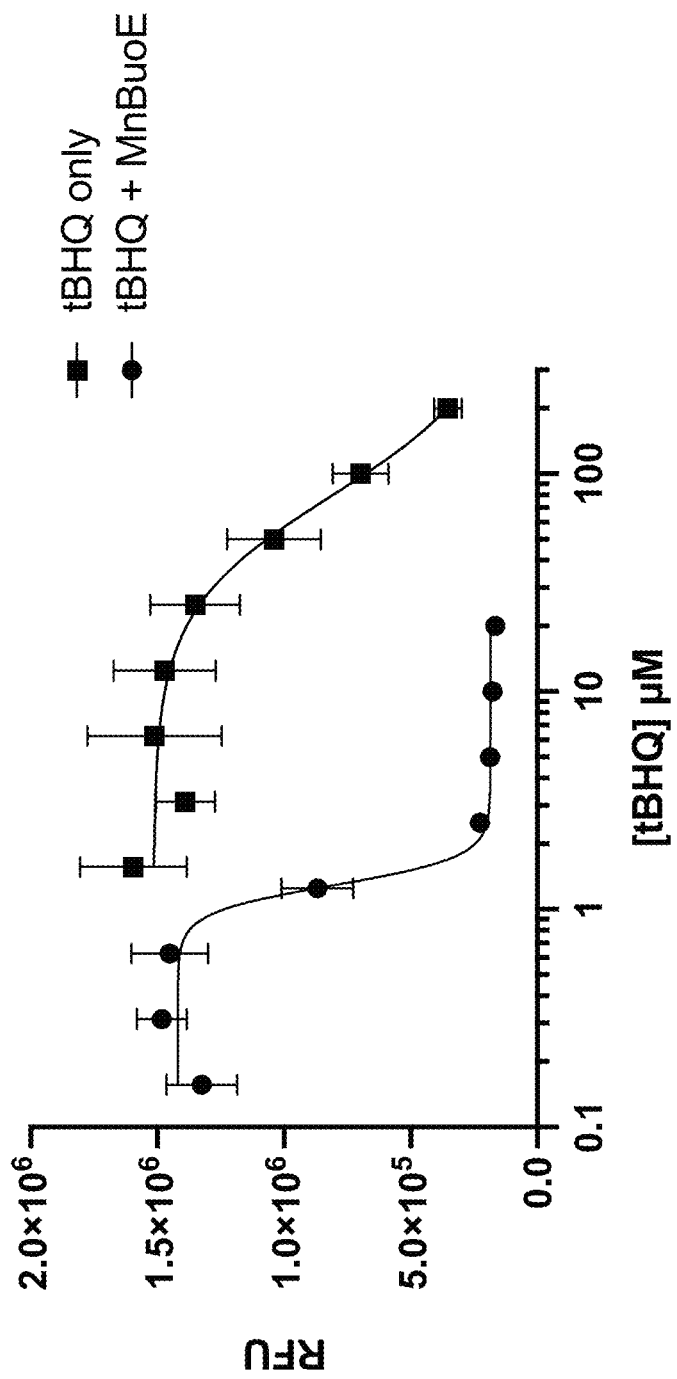
FIG. 16 shows determination of an LC50 value for tBHQ alone and in combination with Mn2BuOE in Jurkat cells.

Referring to FIG. 16, Jurkat cells were treated with the indicated compounds for 24 hours in RPMI with 2% FBS. Live cells were measured using the CellTiter-Fluor dye, which enters living cells and is cleaved by intracellular proteases to release the fluorescent coumarin molecule. Fluorescence was measured on a ClarioStar Plus plate reader in a 96-well plate format with excitation at 390 nm and emission capture at 505 nm. The LC50 was determined in Prism GraphPad using non-linear regression with a four-parameter fit with variable slope. Data are graphed as the average±the standard error, along with the fit.

Figure 17:
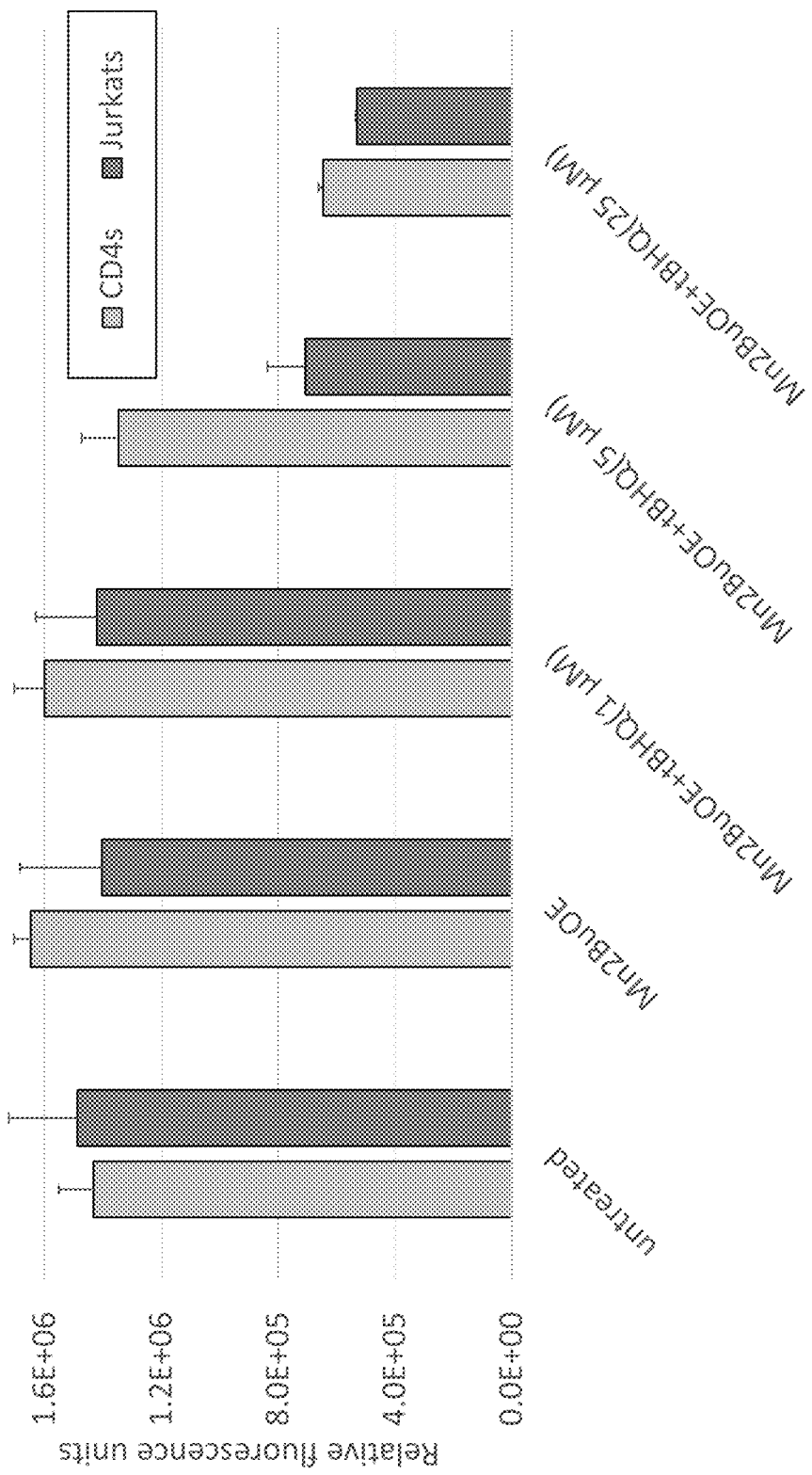
FIG. 17 shows that the combination treatment of tBHQ and MnBuOE is more toxic to leukemic Jurkat CD4 cells than primary CD4 cells.

Referring to FIG. 17, Jurkat cells or CD4+ primary cells were treated for 24 hours with the indicated compounds in RPMI with 10% FBS and 100 IU/mL human IL-2. Live cells were measured using the CellTiter-Fluor dye as for the studies of FIG. 16. Data are plotted as the average±the standard deviation.

Figure 18:
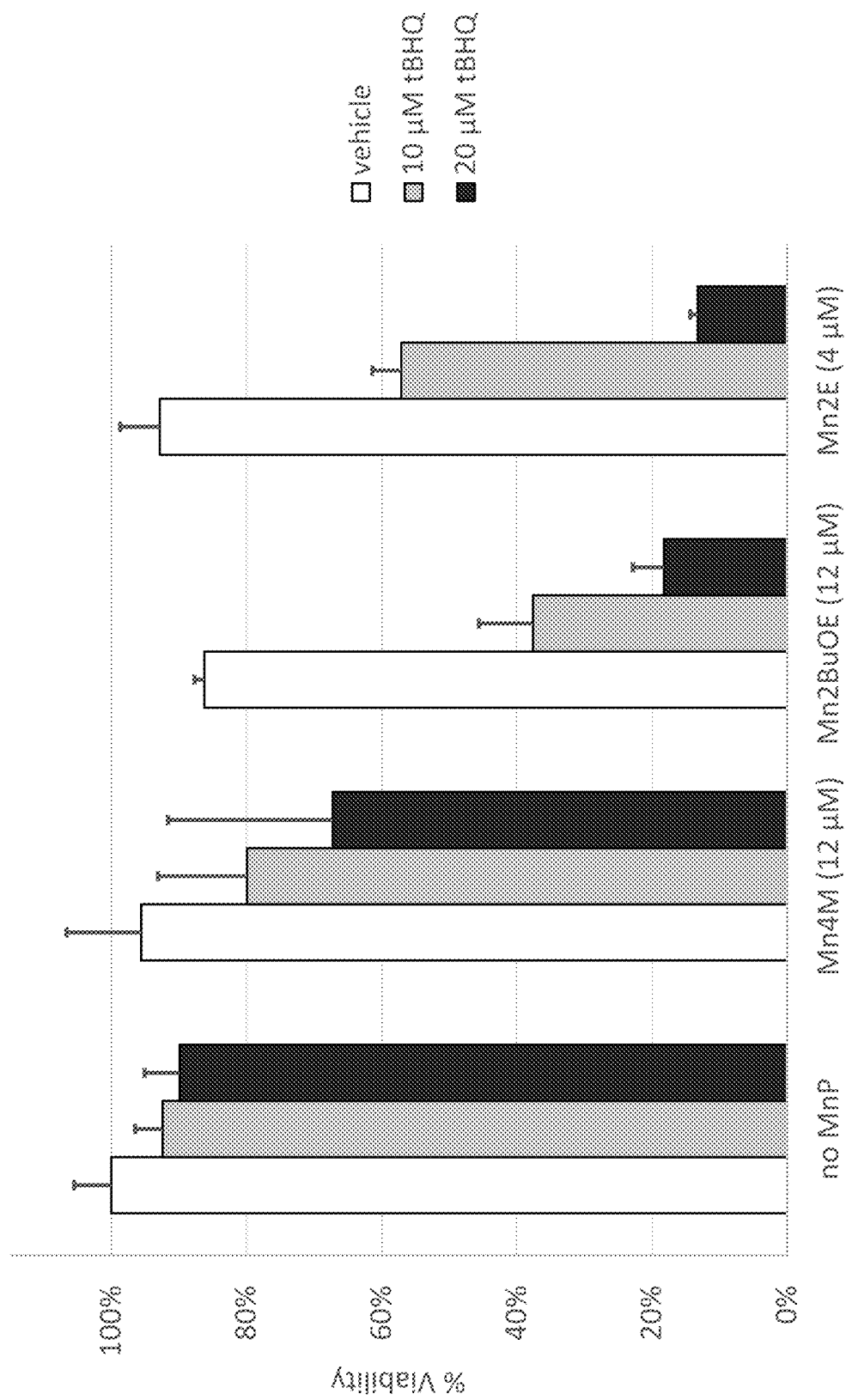
FIG. 18 shows that two manganese porphyrin (MnP) compounds including MNTE-2-PyP and MnTNBuOE-2-PyP are effective at killing MDA-MB-231 breast cancer cells, in combination with tBHQ.
Figure 19:
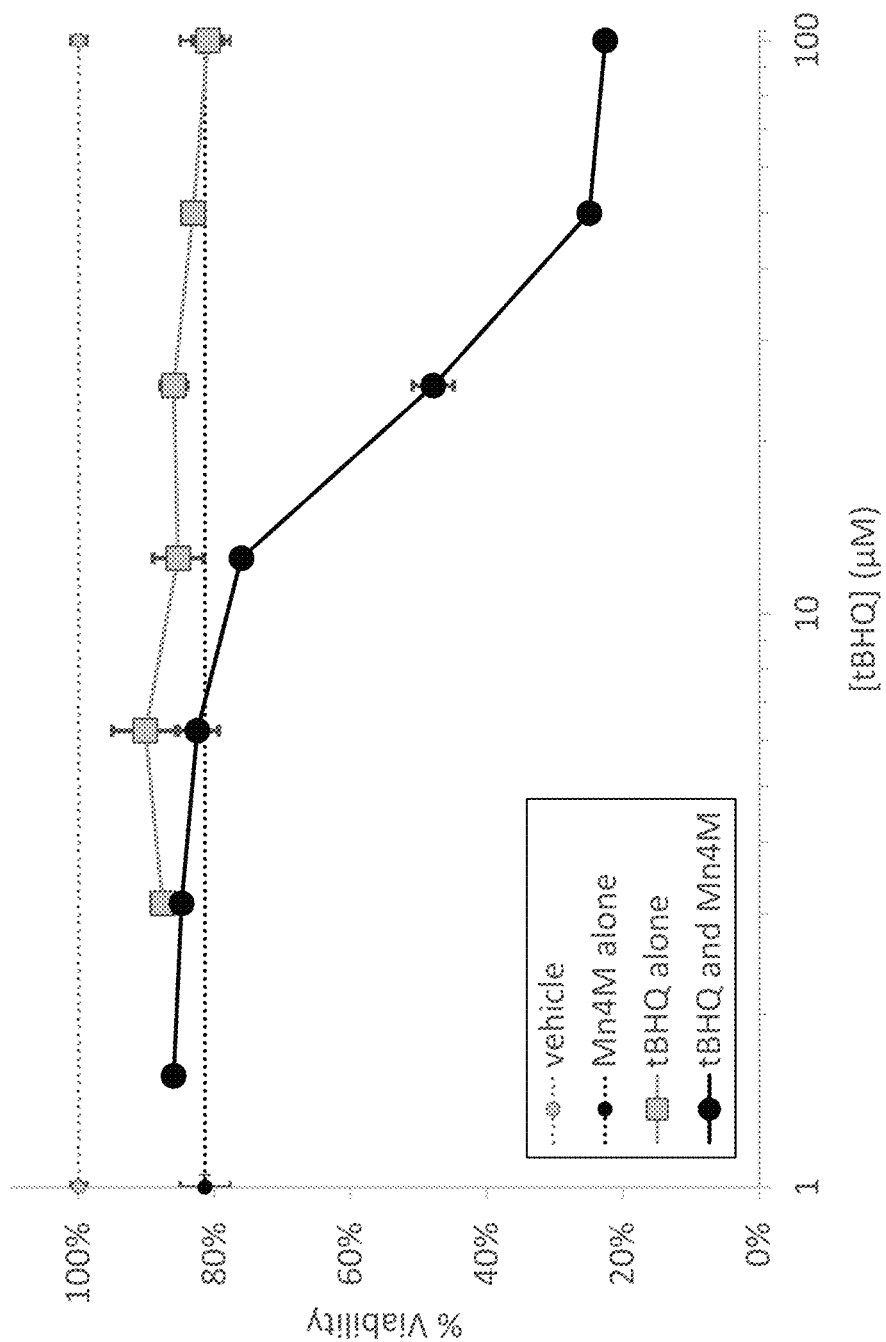
FIG. 19 shows toxicity of tBHQ alone and in combination with Mn4M in MDA-MB-231 cells.
Figure 20:
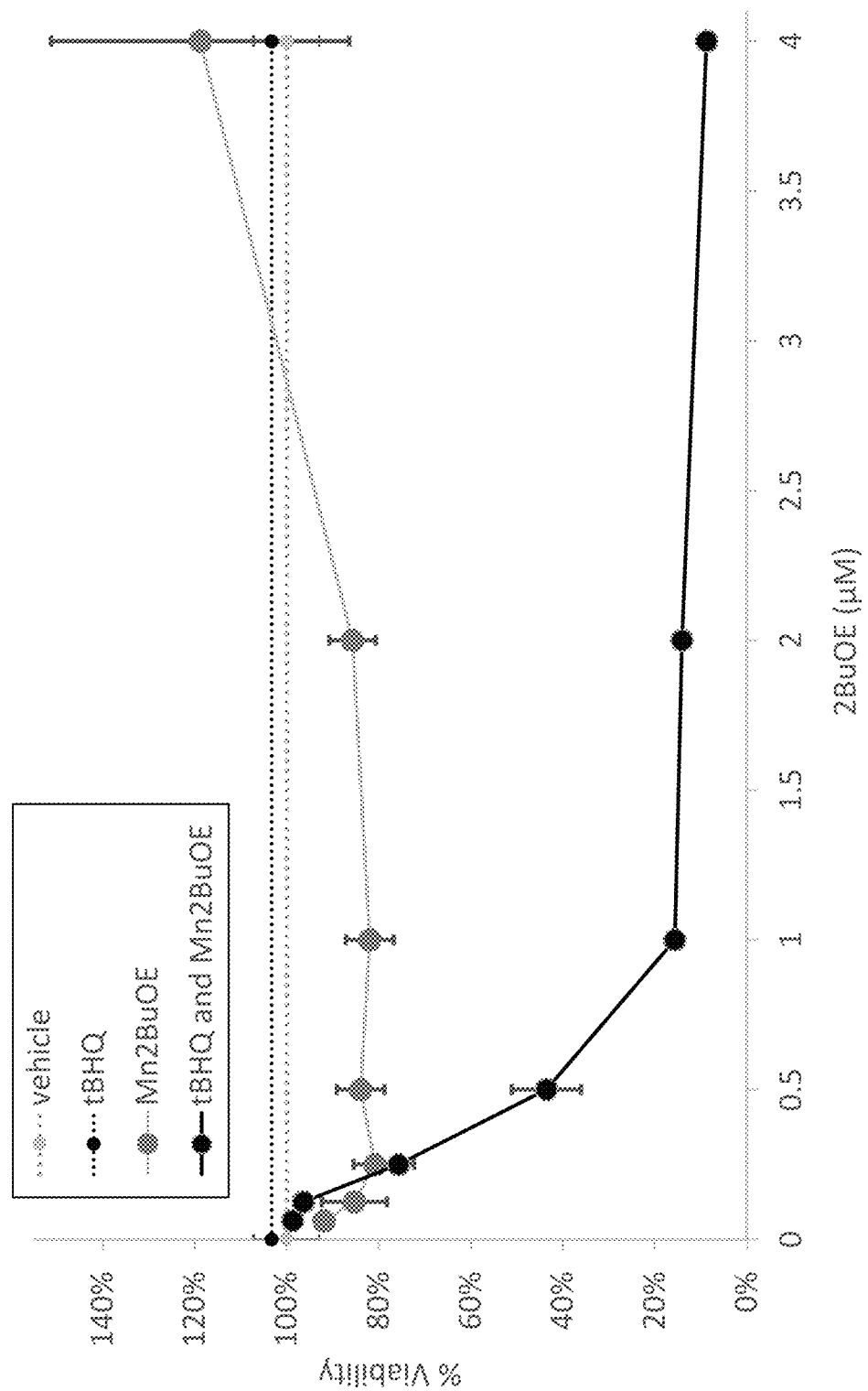
FIG. 20 shows the effect of varying Mn2BuOE concentration, with or without 20 μM tBHQ, on MDA-MB-231 breast cancer cells.

Referring to FIGS. 18, 19, and 20, MDA-MB-231 cells were plated in the interior 60 wells of 96-well plates, with water in the exterior wells, to prevent any edge effects due to evaporation near the plate edges. One day after plating, cells were treated for 24 hours with the indicated compounds in DMEM media with 10% FBS. The percent viability for each sample was determined by first extensively washing cells with phosphate-buffered saline to wash away any non-adherent (non-viable) cells and their contents. Cells were lysed with 0.03% Triton-X100, and total protein was measured using a bicinchoninic acid (BCA) kit, measuring absorbance at 562 nm. Absorbance values were converted to percent viability by first subtracting the absorbance from wells with cells completely killed (by 1.5 mM hydrogen peroxide treatment), then normalizing to the average absorbance of cells treated with vehicle (100% viable). Data are plotted as the average±the standard deviation.

Figure 21:
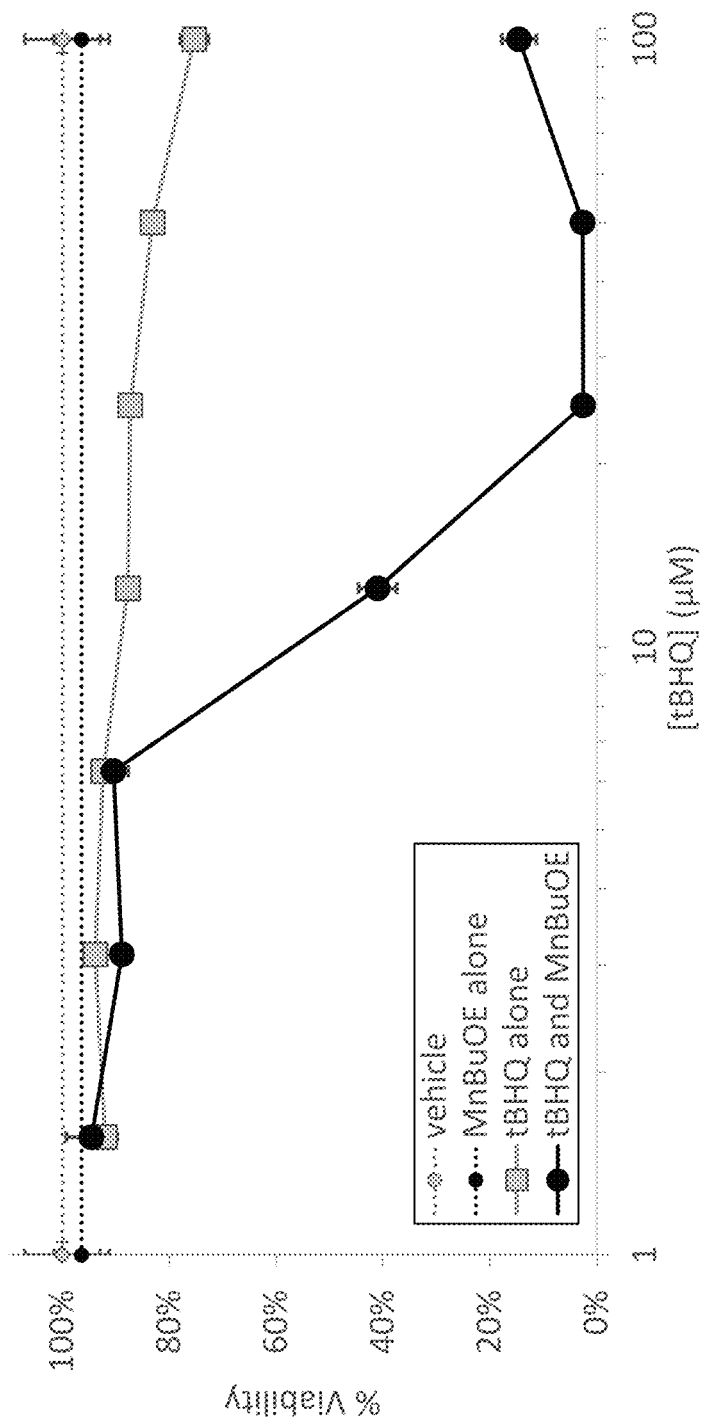
FIG. 21 shows toxicity of tBHQ alone and in combination with Mn2BuOE in PC3 prostate cancer cells.
Figure 22:
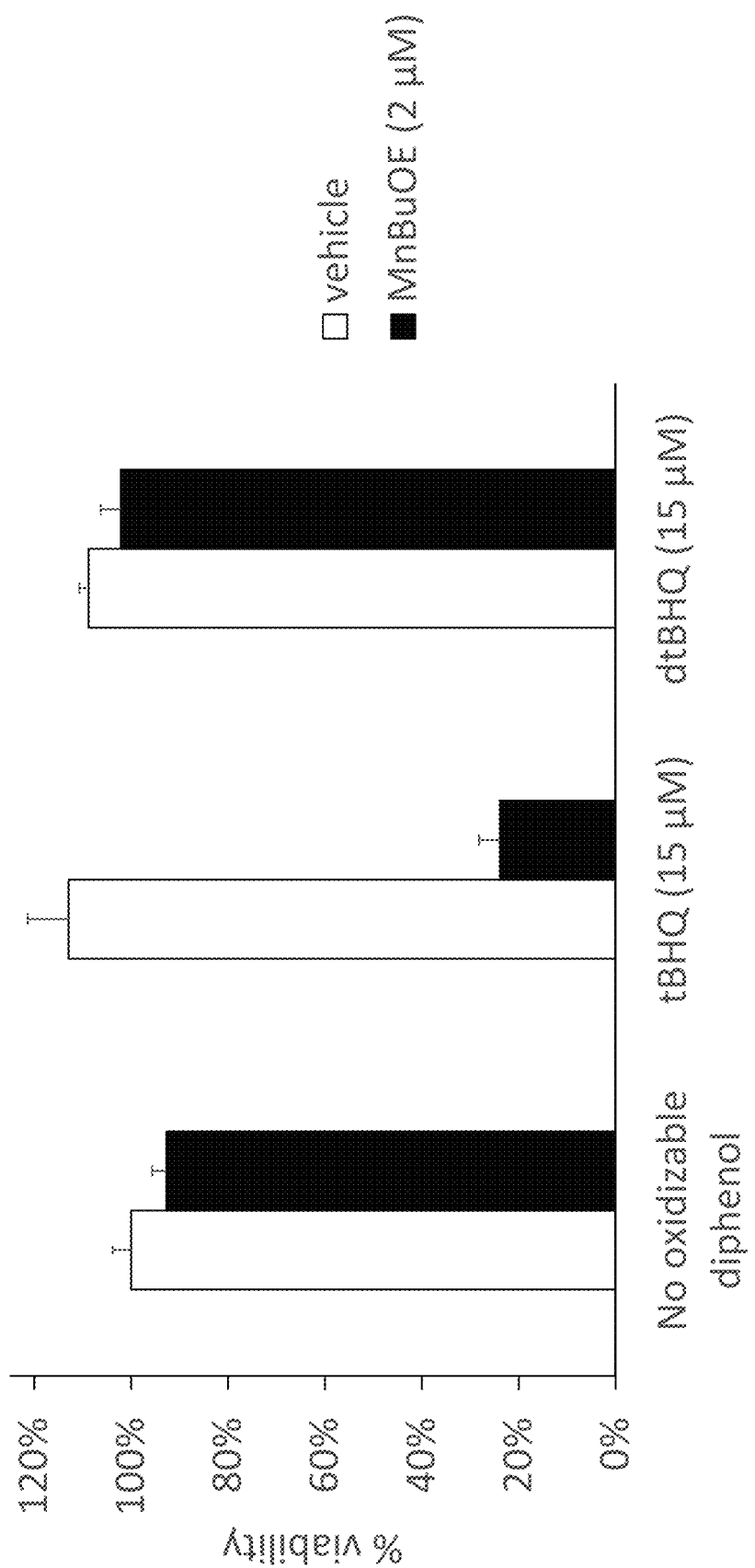
FIG. 22 shows no toxicity of dtBHQ and dtBHQ in combination with MnBuOE to PC3 cells.
Figure 23:
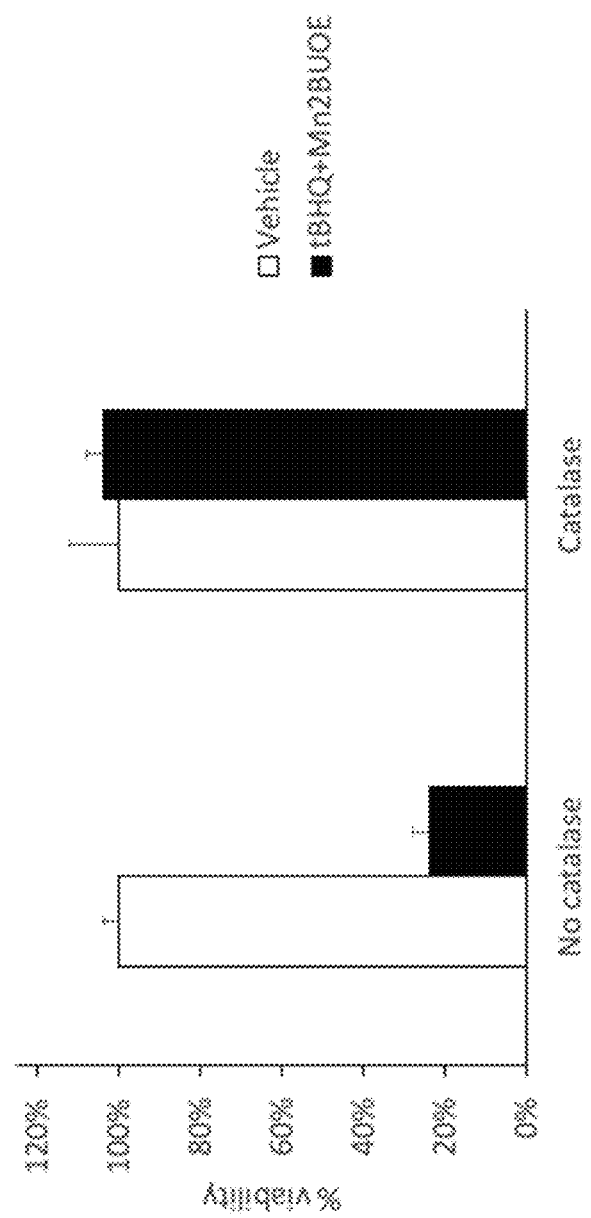
FIG. 23 shows that catalase rescues PC3 prostate cells from toxicity of the tBHQ and Mn2BuOE combination treatment.

Referring to FIGS. 21, 22, and 23, PC3 cells were plated and treated as for MDA-MB-231 cells, but the media used was RPMI with 10% FBS. Percent viability was determined as for MDA-MB-231 cells. For the studies in FIG. 23, catalase was prepared fresh from lyophilized protein in phosphate buffered saline, sterile-filtered, and added with the other treatments to the cells, to a final concentration of 4000 U/mL media.

Figure 4:
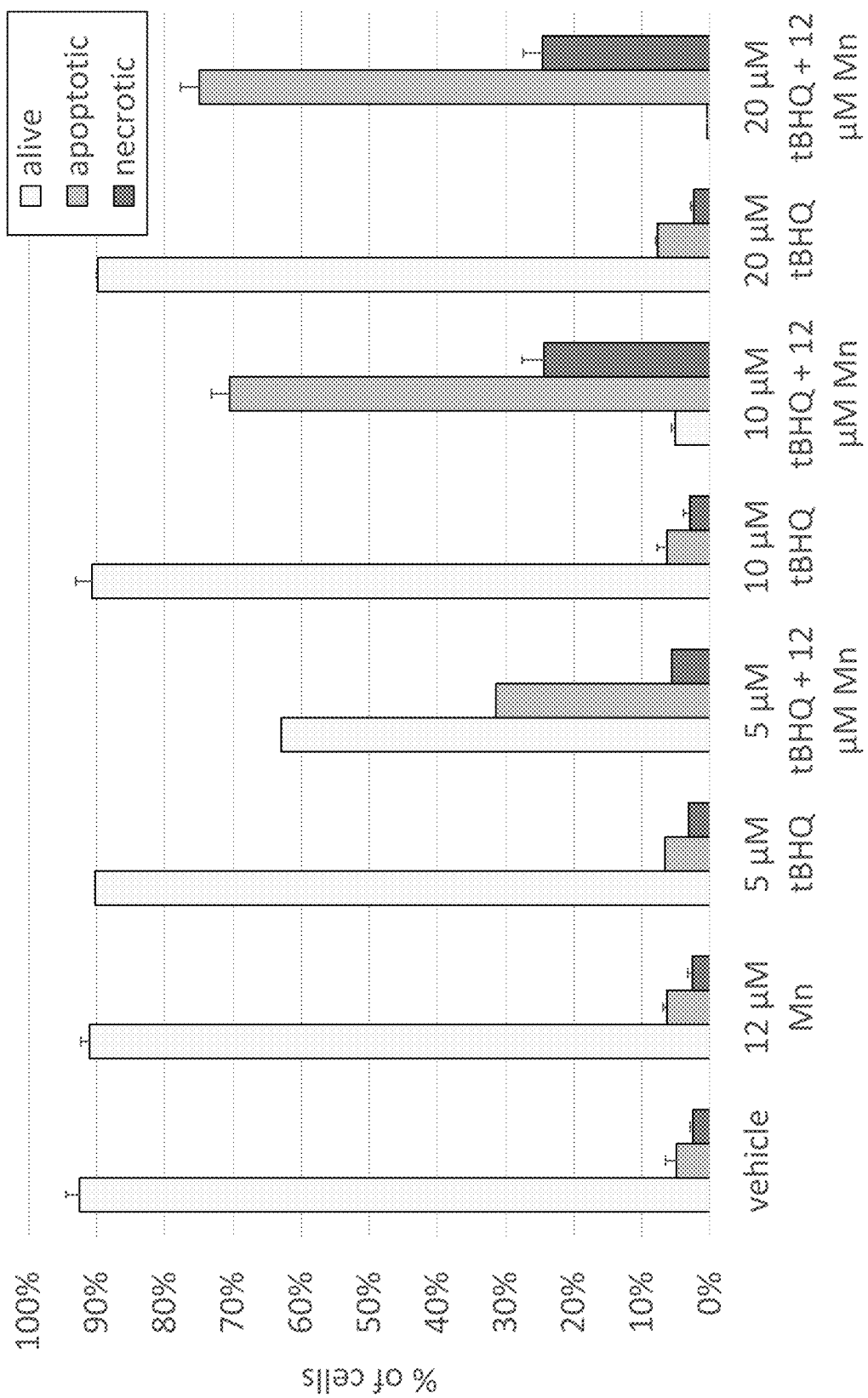
FIG. 4 shows testing results illustrating that a combination of tBHQ and MnTMPyP causes cell death in Jurkat cells (is toxic to Jurkat cells), a CD4+ T-cell leukemic cell line.

FIG. 4 shows that a combination of tBHQ and MnTMPyP causes cell death in Jurkat cells, a CD4+ T-cell leukemic cell line. Causing death of cancer cells such as Jurkat cells means desirable toxicity to the cancer cells.

The combination of tBHQ and MnTMPyP is toxic to Jurkat cells, a CD4+ T-cell leukemic cell line. Jurkat cells were treated with or without tBHQ at the indicated concentrations in the presence or absence of 12 μM MnTMPyP for 4 hours. In FIG. 4 and later figures, "Mn" represents manganese porphyrin such as MnTMPyP. Cells that were alive, apoptotic or necrotic were determined using flow cytometry. Two specimens (biological duplicates) were measured for each sample.

Jurkat cells were largely unaffected by treatment with 5 μM to 20 μM tBHQ for 4 hours, or by treatment with MnTMPyP. However, the combination of tBHQ and the manganese porphyrin was lethal. Approximately 40% of the cells were undergoing apoptosis or were necrotic at 5 μM tBHQ in the combination treatment, and at 20 μM, remaining live cells were negligible. Cell death at each tested tBHQ concentration was primarily apoptotic.

Figure 5:
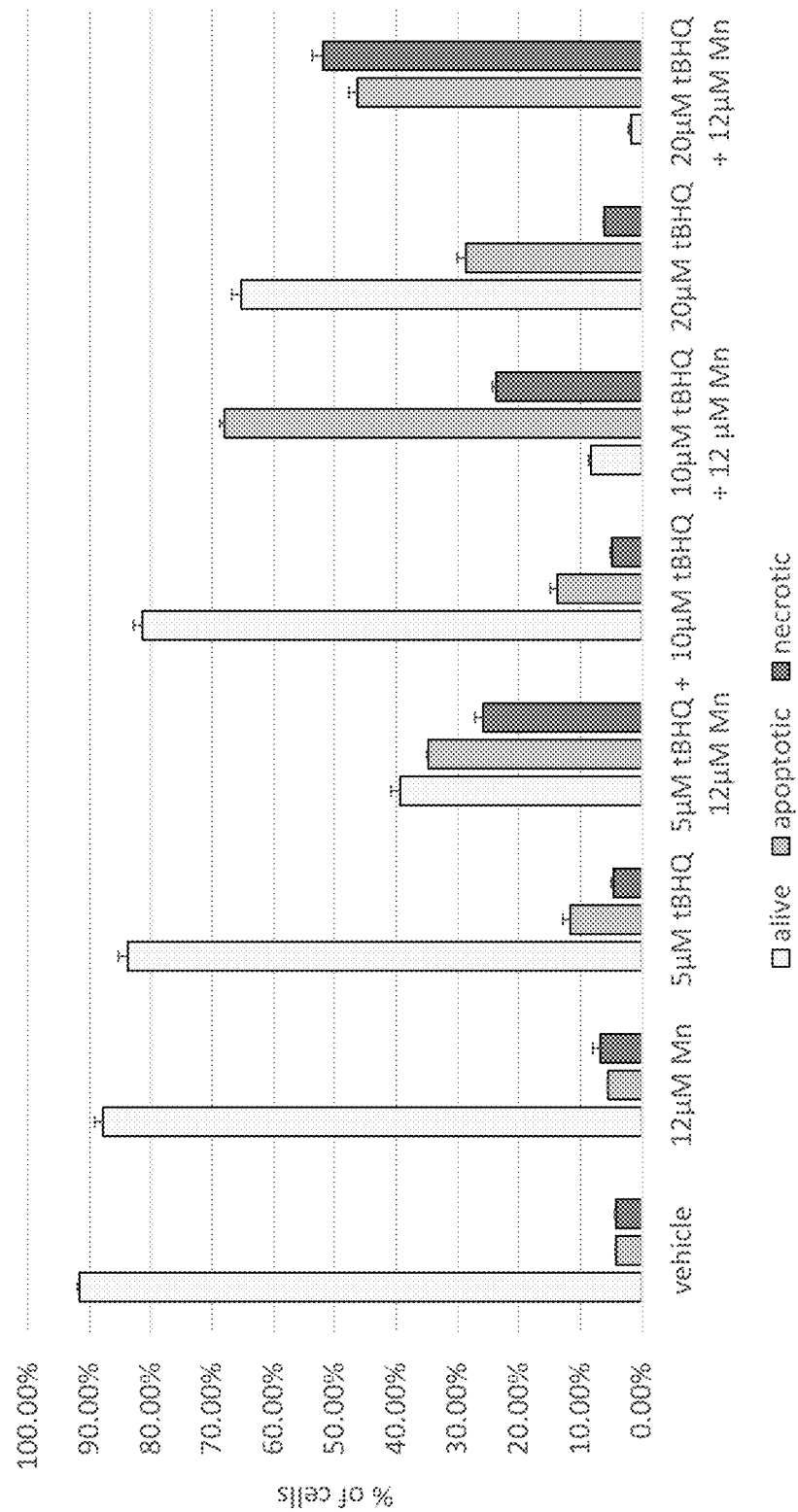
FIG. 5 shows testing results illustrating that the combination of tBHQ and MnTMPyP caused apoptosis and necrosis in NALM6 cells (is toxic to NALM6 cells), a CD19+ B-cell precursor leukemic cell line.

Referring to FIG. 5, the combination of tBHQ and MnTMPyP is toxic to NALM6 cells, a CD19+ B-cell precursor leukemic cell line. NALM6 cells were treated with or without tBHQ at the indicated concentrations in the presence or absence of 12 μM MnTMPyP for 4 hours. Cells that were alive, apoptotic or necrotic were determined using flow cytometry. Biological and technical duplicates (number of specimens n=4) were tested for each sample.

After 4 hours of treatment with a combination of 5 μM tBHQ and 12 μM MnTMPyP, approximately 60% of cells have entered apoptosis or are necrotic. Treatment with either compound individually results in low toxicity. At the highest concentration of tBHQ tested in combination with the manganese porphyrin, 20 μM, almost all cells are apoptotic or necrotic.

Figure 6:
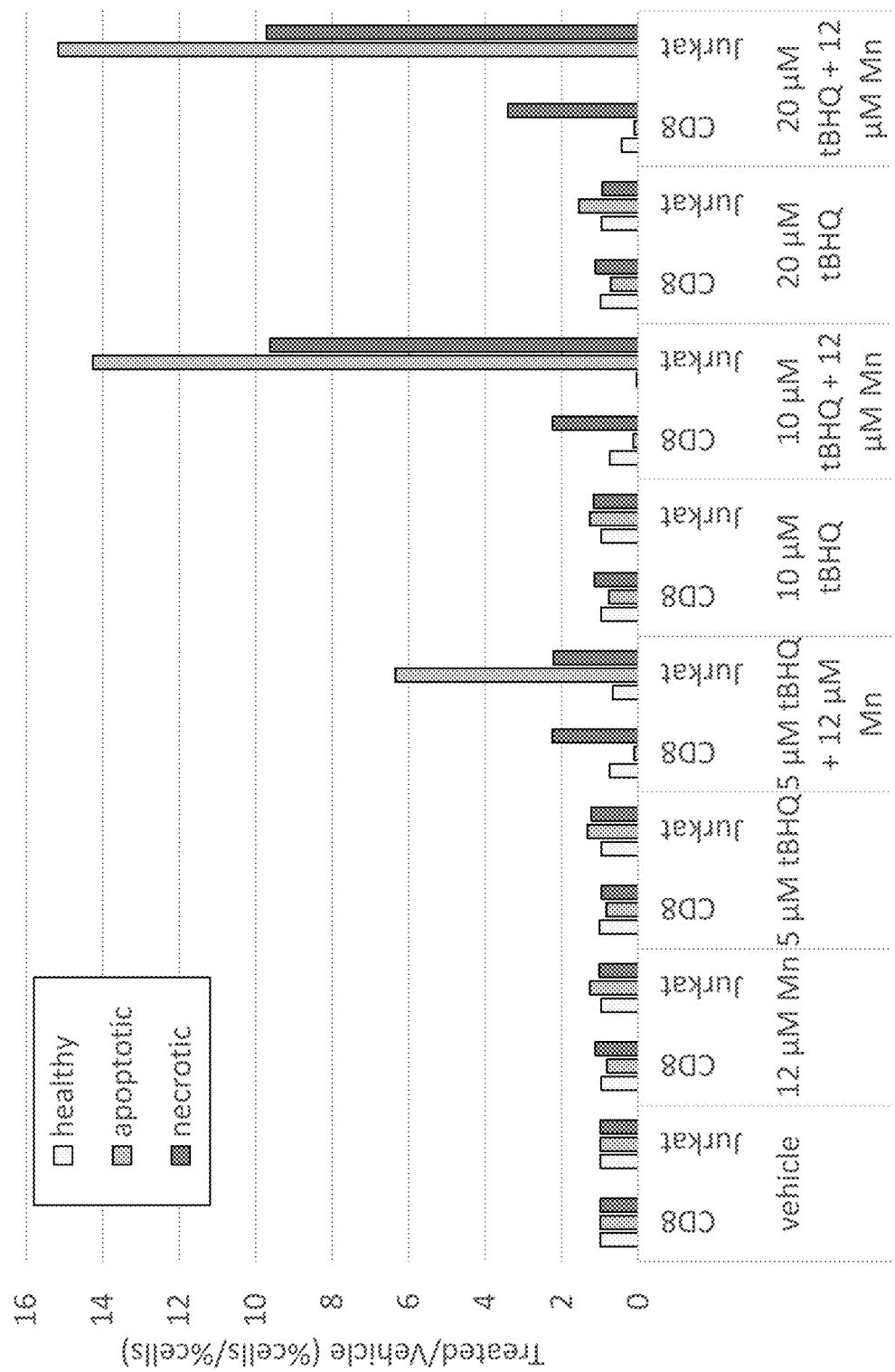
FIG. 6 illustrates testing results showing that the combination of tBHQ and MnTMPyP is relatively much less toxic to primary CD8+ T cells than to Jurkat cells.

Referring to FIG. 6, the combination of tBHQ and MnTMPyP is less toxic to primary CD8+ T cells than to Jurkat cells. In single day, Jurkat cells or CD8+ cells were treated and analyzed as for FIG. 4. Fold change relative to the untreated condition (vehicle) was calculated for alive (labelled as "healthy"), apoptotic, and necrotic CD8$^+$ cells and Jurkat cells. Two specimens (biological duplicates, n=2) were measured for each sample.

After 4 hours of treatment with a combination of 10 μM tBHQ and 12 μM MnTMPyP, there are approximately 14 times more Jurkat cells in apoptosis compared to treatment with the vehicle, and there are approximately 10 times more Jurkat cells in necrosis. In comparison, after 4 hours of treatment pf with the same combination, there are only 2 times as many CD8+ cells in necrosis and in fact fewer cells in apoptosis, compared to treatment with vehicle. The effect is dose-dependent.

Figure 7:
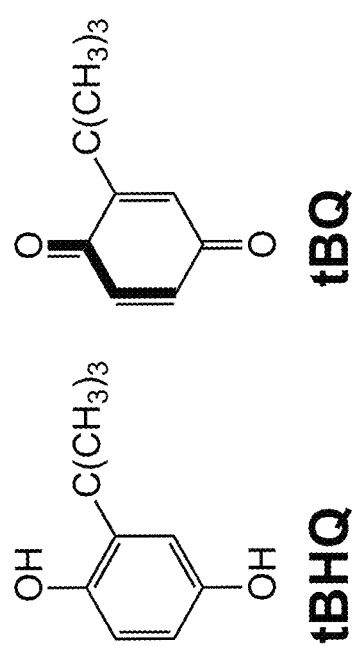
FIG. 7 shows the structures of tert-butyl hydroquinone (tBHQ) and tert-butyl quinone (tBQ).

Referring to FIG. 7, the chemical structures of tBHQ and tBQ are shown. tBHQ is a hydroquinone and is used as an antioxidant in foods. tBQ is the quinone formed upon oxidation of tBHQ, a chemical transformation catalyzed by MnTMPyP as shown in FIGS. 2-3. The electrophilic alpha, beta unsaturated carbonyl moiety in the structure of tBQ, shown in bold, is likely responsible for the toxicity of the quinone.

Figure 8:
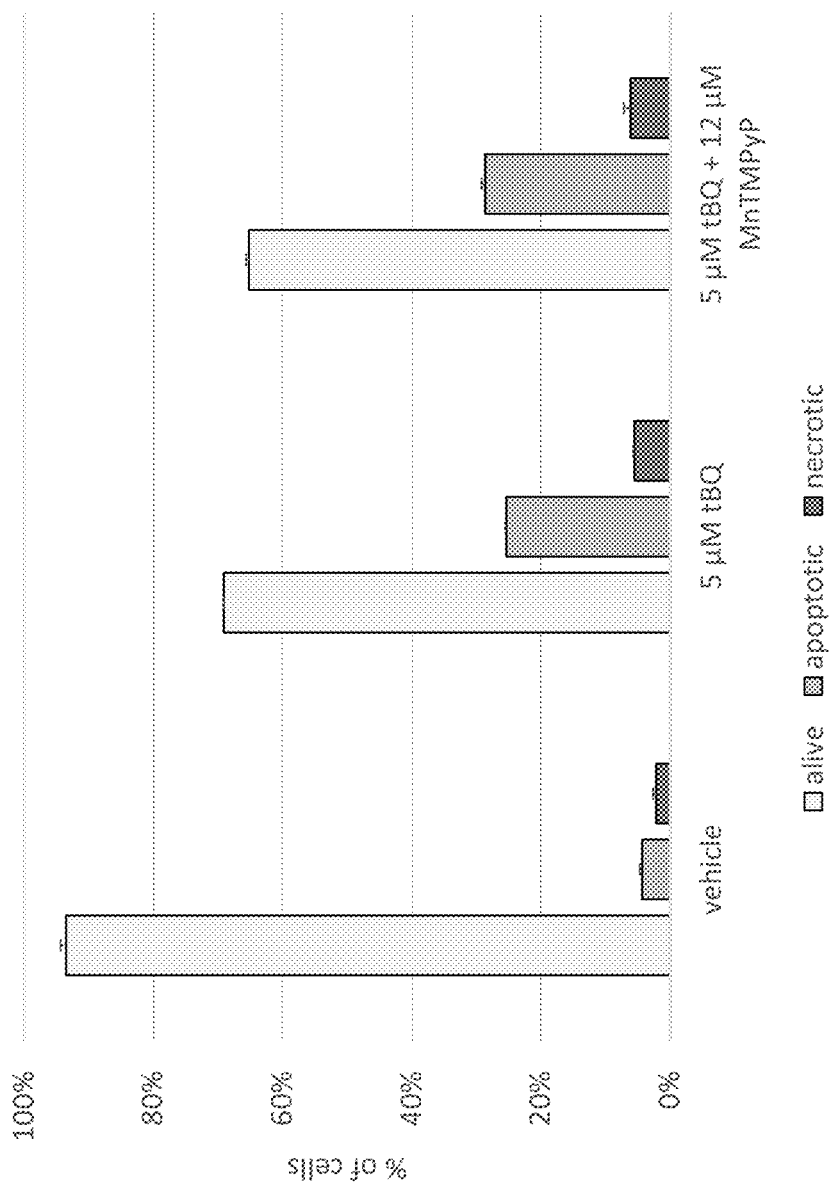
FIG. 8 shows testing results illustrating that tBQ alone causes cell death in Jurkat cells and has similar toxicity to Jurkat cells as does the combination of tBHQ and MnTMPyP.

Referring to FIG. 8, tBQ alone has similar toxicity to Jurkat cells as does the combination of tBHQ and MnTMPyP.

Jurkat cells were treated with or without 5 μM tBQ at the indicated concentrations in the presence or absence of 12 μM MnTMPyP for 4 hours. Cells that were alive, apoptotic or necrotic were determined using flow cytometry, with n=2 (biological duplicates). Comparing FIG. 8 with FIG. 4, tBQ alone has similar toxicity to Jurkat cells as does the combination of tBHQ with MnTMPyP. These data support the hypothesis that the quinone (see FIGS. 3 and 7) is the toxic agent. In addition, the inclusion of MnTMPyP with tBQ does not alter the result compared to tBQ alone, further supporting this hypothesis.

Referring to FIG. 9, tBQ alone is sufficient to cause apoptosis in Jurkat cells. The result is unaffected by inclusion of MnTMPyP. Jurkat cells were treated with tBQ or tBHQ at 5 μM in the presence or absence of 12 μM MnTMPyP for 4 hours. Levels of mitochondrial superoxide were quantified using MitoSOX Red and measured on the flow cytometer, with n=2 (technical replicates).

While tBHQ alone causes no mitochondrial ROS formation, as shown in comparison with vehicle, the combination treatment of tBHQ+MnTMPyP does. A similar level of mitoROS is caused by tBQ, and this is unaffected by MnTMPyP. These data support the hypothesis that the quinone is the toxic agent and that part of its mechanism is the generation of ROS, including in the mitochondria.

Figure 10:
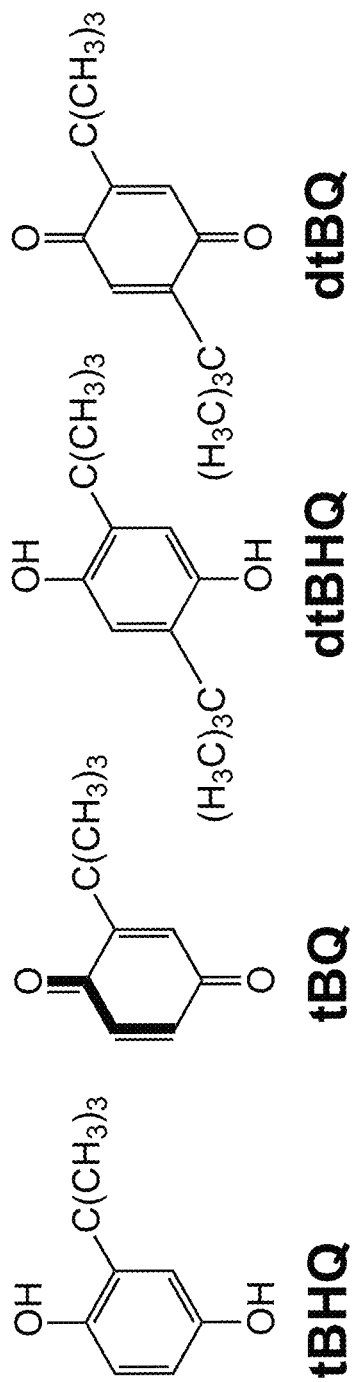
FIG. 10 shows the structures of tBHQ, tBQ, 2,5-di-tert-butyl hydroquinone (dtBHQ), 2,5-di-tert-butyl quinone (dtBQ).

FIG. 10 shows the structures of tert-butyl hydroquinone (tBHQ), tert-butyl quinone (tBQ), 2,5-di-tert-butyl hydroquinone (dtBHQ), 2,5-di-tert-butyl quinone (dtBQ). As compared with tBHQ and its oxidized quinone form, tBQ, dtBHQ and dtBQ contain an extra tert-butyl arm which sterically blocks the oxidized product, dtBQ, from acting as an electrophile. The additional tert-butyl group on dtBQ blocks electrophilic addition to the dtBQ quinone, hence dtBQ is not electrophilic. dtBHQ and dtBQ are usual in testing the hypothesis that the electrophilic alpha, beta unsaturated carbonyl moiety in the structure of tBQ, shown in bold, is likely responsible for the toxicity of the quinone.

Figure 11:
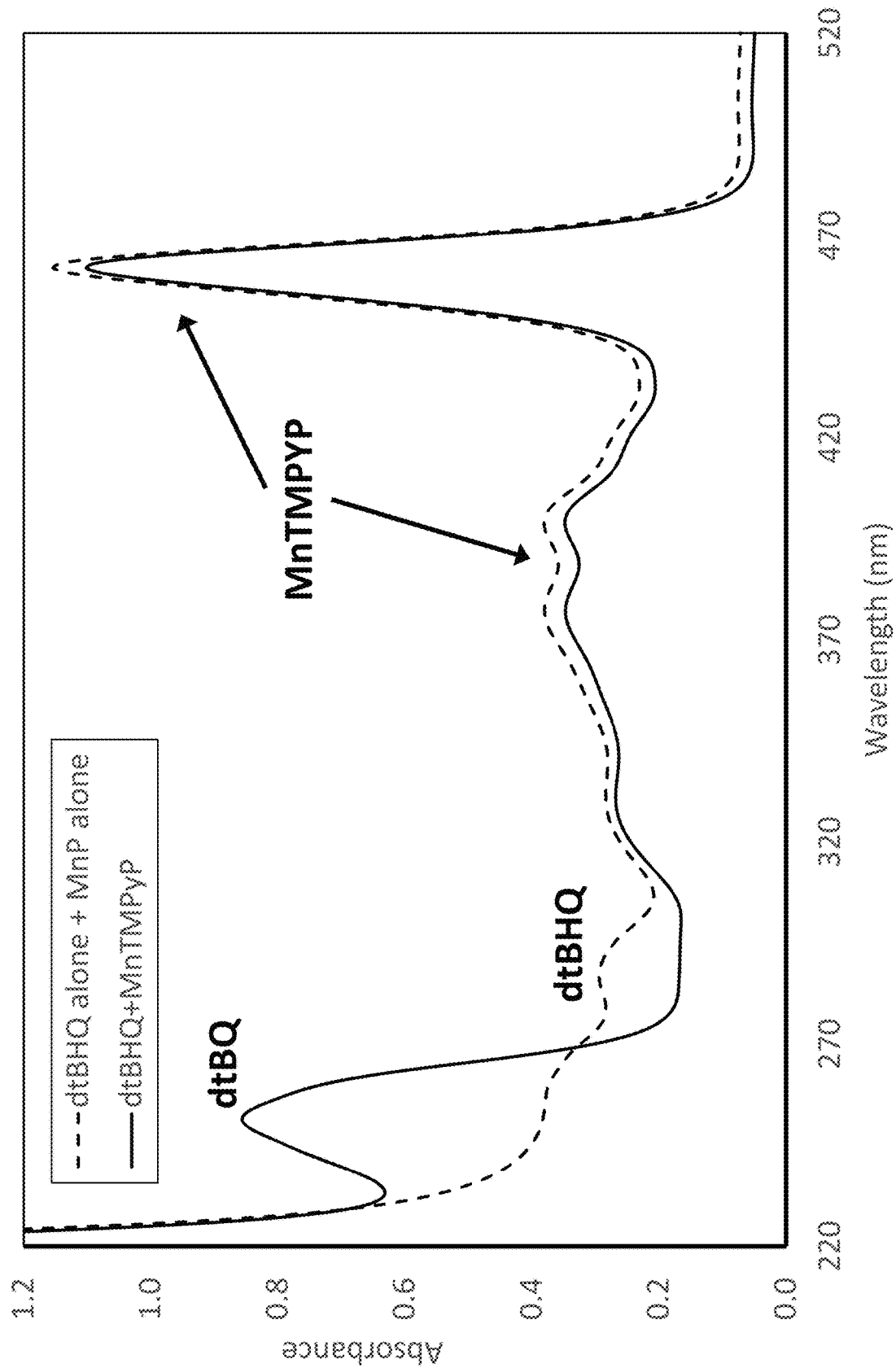
FIG. 11 are ultra-violet/visible light spectroscopy results showing that MnTMPyP catalyzes oxidation of dtBHQ to dtBQ.

Referring to FIG. 11, ultra-violet/visible light spectroscopy results show that MnTMPyP catalyzes oxidation of dtBHQ to dtBQ.

As for tBHQ in FIG. 4, MnTMPyP readily catalyzes the oxidation of dtBHQ to dtBQ, supporting the usefulness of dtBHQ as a means of determining the mechanism of toxicity of the tBHQ/MnTMPyP combination.

Figure 12:
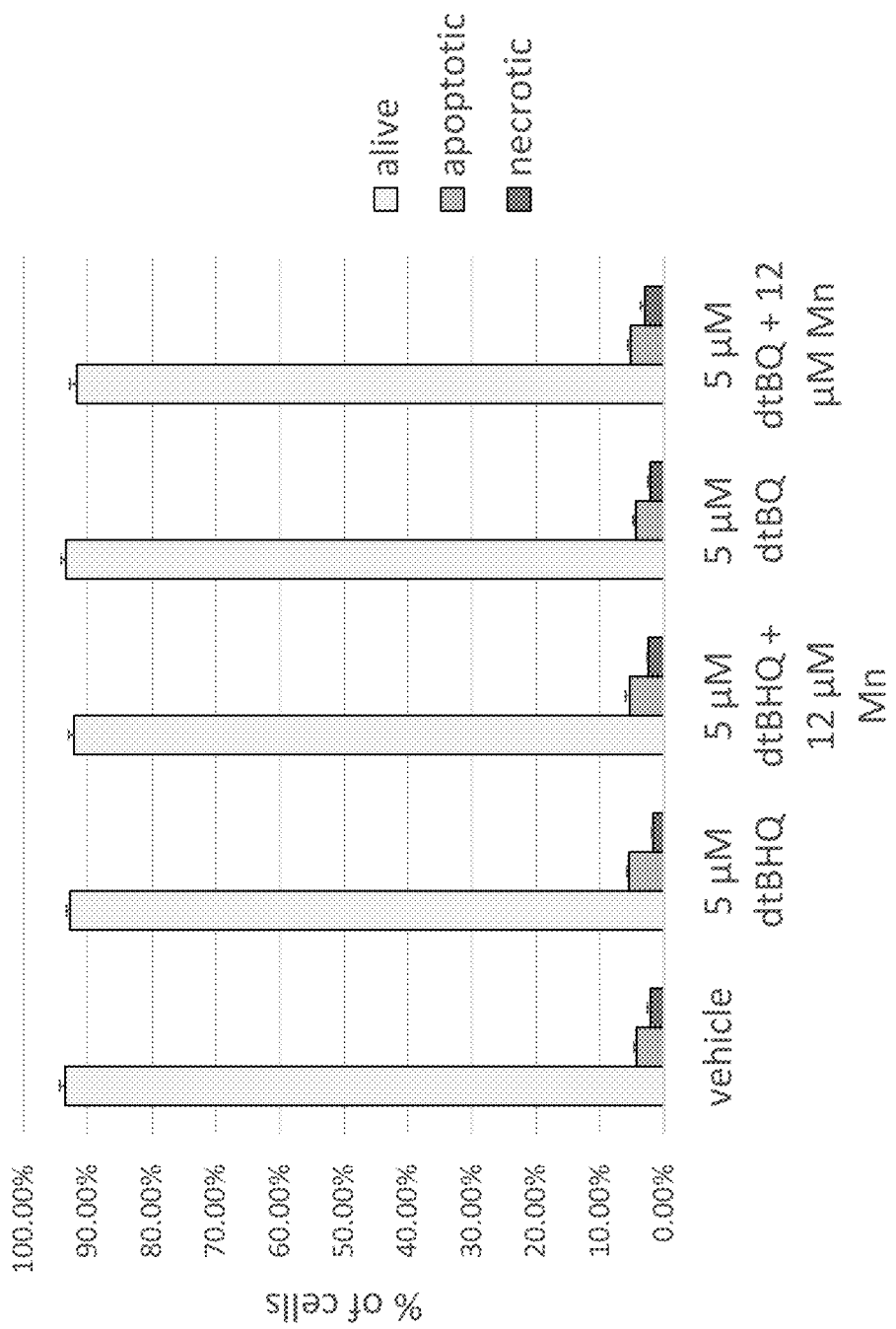
FIG. 12 shows the testing results illustrating that the combination of dtBHQ and MnTMPyP does not harm Jurkat cells, indicating that the electrophilic quinone tBQ, rather than hydrogen peroxide, is responsible for Jurkat cell death.

Referring to FIG. 12, unlike tBHQ, dtBHQ has no toxicity to Jurkat cells in combination with MnTMPyP. Jurkat cells were treated with or without 5 μM dtBHQ or dtBQ in the presence or absence of 12 μM MnTMPyP for 4 hours. Cells that were alive, apoptotic or necrotic were determined using flow cytometry, with n=2 (biological duplicates).

Comparing the results in FIG. 12 with those in FIG. 4, there was no toxicity of dtBHQ in combination with MnTMPyP to Jurkat cells. Similarly, there is no toxicity of dtBQ. These data support the hypothesis that tBQ is the toxic agent, rather than ROS generated by the oxidation of tBHQ to tBQ (see also FIG. 33).

Referring to FIG. 13, dtBHQ, dtBHQ in combination with MnTMPyP, and dtBQ all show no production of ROS in the mitochondria. Jurkat cells were treated with dtBQ or dtBHQ at 5 μM in the presence or absence of 12 μM MnTMPyP for 4 hours. Levels of mitochondrial superoxide were quantified using MitoSOX Red and measured on the flow cytometer, with n=2 (technical replicates).

The lack of an effect of these compounds with an additional tert-butyl arm blocking the electrophilic nature of the quinone supports the same hypothesis as for FIG. 12.

Figure 14:
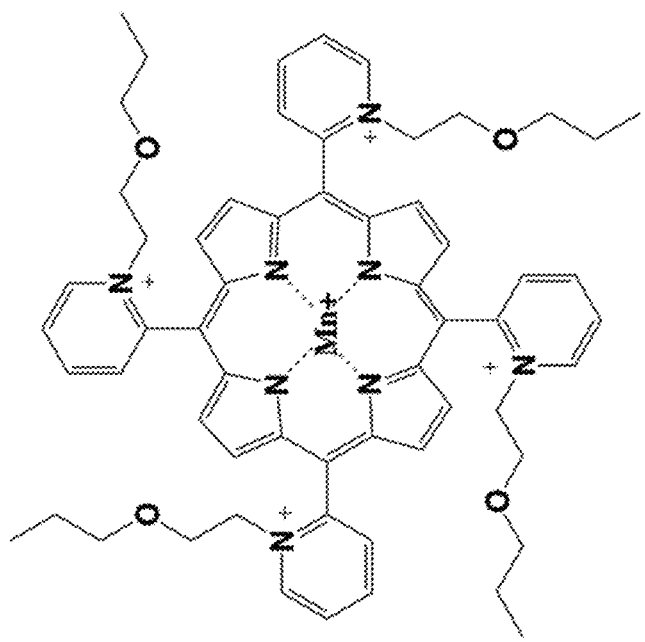
FIG. 14 shows structures of manganese (III) meso-tetrakis (N-ethylpyridinium yl)porphyrin (MNTE-2-PyP, or Mn2E in the graph labeling) and manganese (III) meso-tetrakis(N-n-butoxyethyl-pyridinium-2yl)porphyrin (MnTNBuOE-2-PyP, or Mn2BuOE for graph labeling), which are two exemplary manganese porphyrins in accordance with some embodiments.
Figure 14:
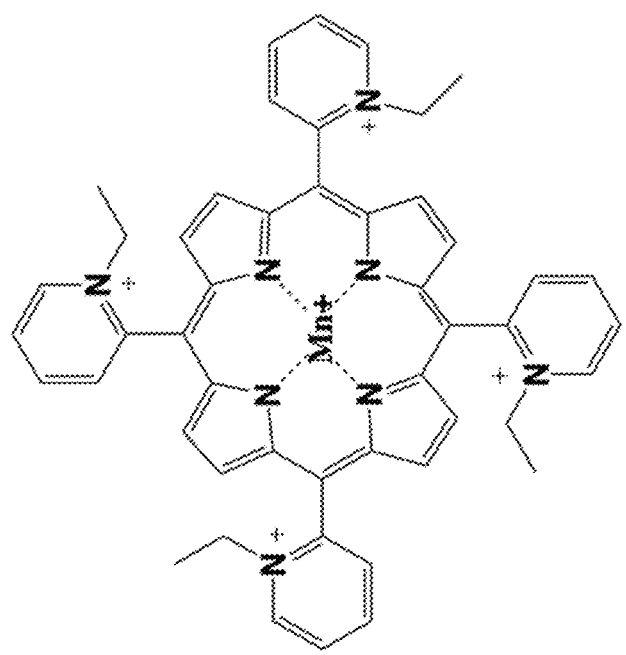

Referring to FIG. 14, the structures of two exemplary manganese porphyrin compounds are shown. The two compounds are manganese (III) meso-tetrakis(N-ethylpyridinium-2-yl)porphyrin (MNTE-2-PyP, or Mn2E in the graph labeling) and manganese (III) meso-tetrakis(N-n-butoxyethyl-pyridinium-2yl)porphyrin (MnTNBuOE-2-PyP, or Mn2BuOE for graph labeling), which are two exemplary manganese porphyrins in accordance with some embodiments. These two exemplary manganese porphyrin compounds are manganese porphyrins in clinical trials.

Figure 15:
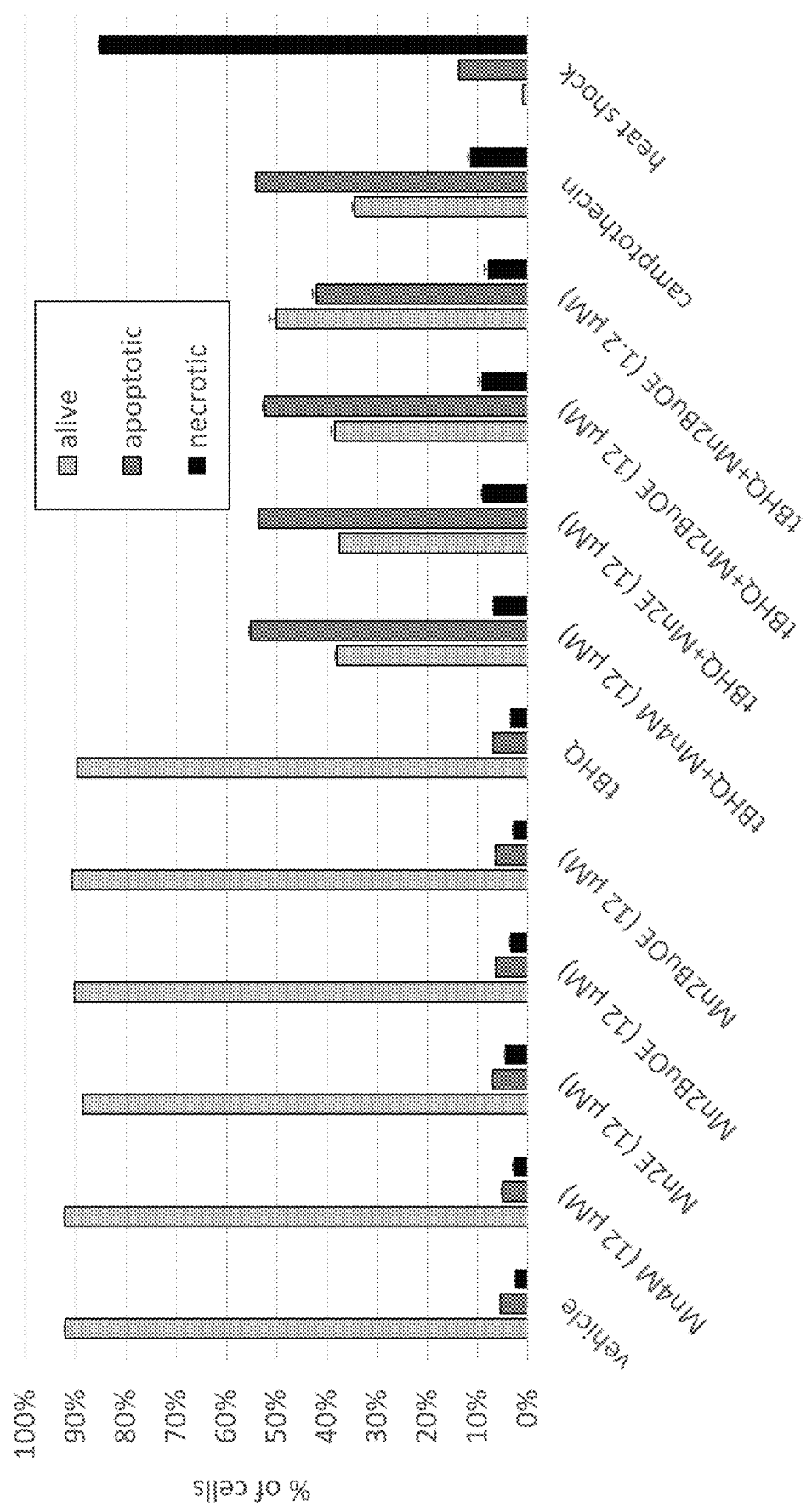
FIG. 15 shows comparison of Jurkat cell death upon exposure to Mn2E and Mn2BuOE with that of exposure to MnTMPyP (labelled as Mn4M in the drawings).

Referring to FIG. 15, Jurkat cell death upon exposure to MNTE-2-PyP and MnTNBuOE-2-PyP (labelled as Mn2E and Mn2BuOE, respectively, in FIG. 15) are compared with that of exposure to Mn4M. Jurkat cells were treated for four hours with or without 5 µM tert-butyl hydroquinone (tBHQ) in the presence or absence of the three manganese porphyrin (MnP) compounds at the indicated concentrations. Positive controls for apoptosis (camptothecin) and necrosis (heat shock) are included. Cells that were alive, apoptotic or necrotic were determined using flow cytometry, with n=2 (technical duplicates).

All three manganese porphyrin show no toxicity to Jurkats when the cells are treated with these individually at the indicated concentrations. In contrast, 5 µM tBHQ in combination with each manganese porphyrin causes both apoptotic and necrotic cell death. The extent and type of cell death was almost identical for each manganese porphyrin at 12 µM. MnBuOE was almost as effective at 1.2 µM as it was at 12 µM.

Referring to FIG. 16, lethal concentration 50 (LC50) values were determined for tBHQ alone and in combination with Mn2BuOE in Jurkat cells. Jurkat cells were treated with or without tBHQ at the indicated concentrations in the presence or absence of 2 µM MnTNBuOE-2-PyP (labeled as Mn2BuOE in FIG. 16) for 24 hours. The relative number of viable cells in a sample was determined using CellTiter-Fluor dye with relative fluorescence units (RFU). The LC50 was determined in Prism GraphPad using non-linear regression with a four-parameter fit with variable slope, with n=6 (biological replicates). The LC50 value for a compound is the concentration required to kill half of the cells tested after a specified test duration such as 24 hours.

The LC50 value for tBHQ in the presence of Mn2BuOE in Jurkat cells is 1.29±0.04 µM. In contrast, the LC50 value for tBHQ alone is 80±30 04. The LC50 value for tBHQ alone has a higher standard deviation, which might be caused by the limitation on solubility of tBHQ in media at higher concentrations.

Referring to FIG. 17, the combination treatment of tBHQ and MnTNBuOE-2-PyP (labeled as Mn2BuOE in FIG. 17) is more toxic to leukemic Jurkat CD4+ cells than primary CD4 cells. Jurkat or CD4+ primary cells were treated with or without tBHQ at the indicated concentrations in the presence or absence of 2 µM Mn2BuOE for 24 hours. The relative number of viable cells in a sample was determined using CellTiter-Fluor dye with relative fluorescence units (RFU), with n=6 (biological replicates).

Given that Jurkat cells are CD4+, primary CD4+ cells were tested side-by-side with Jurkat cells to compare the relative toxicity of the treatment to each cell type. At 5 tBHQ with the manganese porphyrin, primary CD4+ cells were largely unaffected, while Jurkat cells showed a large decrease in viable cells. Jurkat CD4+ cell line was established from a patient with T cell leukemia, while the primary CD4+ cells are from a healthy, cancer-free volunteer. Both cell types are CD4 T lymphocytes, known as helper T cells. The Jurkats are a model for acute T cell leukemia. The fact that the Jurkat cells are more susceptible to the combination treatment than the primary CD4+ cells provides preclinical evidence that the combination treatment is targeted to kill cancer cells preferentially over normal, healthy cells.

Referring to FIG. 18, two manganese porphyrin compounds including manganese (III) meso-tetrakis(N-ethylpyridinium-2-yl)porphyrin (MNTE-2-PyP, or Mn2E in the graph labeling) and manganese (III) meso-tetrakis(N-n-butoxyethyl-pyridinium-2yl)porphyrin (MnTNBuOE-2-PyP, or Mn2BuOE for graph labeling) are also effective at killing MDA-MB-231 breast cancer cells, in combination with tBHQ. MDA-MD-231 cells were treated for 24 hours with or without tBHQ at the indicated concentrations in the presence or absence of the three manganese porphyrin compounds described herein at the indicated concentrations. Percent viability was determined as for MDA-MB-231 cells, with n=6 (biological replicates).

Both Mn2TE2 and Mn2BuOE show higher efficacy at killing breast cancer cells than MnTM4PyP, when combined with tBHQ. None of the three manganese porphyrins showed significant toxicity as a single treatment.

Referring to FIG. 19, toxicity of tBHQ alone and in combination with MnTMPyP (labeled as Mn4M in FIG. 19) in MDA-MB-231 cells were evaluated. MDA-MD-231 cells were treated for 24 hours with or without tBHQ at the indicated concentrations in the presence or absence of 12 µM MnTMPyP. Percent viability was determined as for MDA-MB-231 cells. The LC50 was determined by non-linear regression with a four-parameter fit with variable slope, with n=6 (biological replicates).

The LC50 value for tBHQ in the presence of MnTMPyP (i.e., Mn4M) in MDA-MB-231 cells is 20.±2 µM. In contrast, the LC50 value for tBHQ alone >100 with no toxicity observed at 100 µM.

Referring to FIG. 20, the effect of various concentration of MnTNBuOE-2-PyP (labeled as Mn2BuOE in FIG. 20), with or without 20 µM tBHQ, on MDA-MB-231 breast cancer cells was studied. MDA-MB-231 breast cancer cells were treated for 24 hours with or without 20 µM tBHQ in the presence or absence of Mn2BuOE at the indicated concentrations. Percent viability was determined as for MDA-MB-231 cells, with n=6 (biological replicates). Mn2BuOE alone is not toxic at tested concentrations and is active at concentrations less than 1 µM.

Referring to FIG. 21, toxicity of tBHQ alone and in combination with MnTNBuOE-2-PyP (labeled as Mn2BuOE in FIG. 21) in PC3 prostate cancer cells were studied. PC3 prostate cancer cells were treated for 24 hours with or without tBHQ at the indicated concentrations in the presence or absence of 2 µM Mn2BuOE. Percent viability was determined as for MDA-MB-231 cells. The LC50 value was determined using plot.ly by non-linear regression with a four-parameter fit with variable slope, with n=6 (biological replicates).

The LC50 value for tBHQ in the presence of Mn2BuOE in PC3 prostate cancer cells is 16±7 µM. In contrast, the LC50 value for tBHQ alone >100 µM.

Referring to FIG. 22, dtBHQ and dtBHQ in combination with MnTMPyP both show no toxicity to PC3 prostate cancer cells. PC3 prostate cancer cells were treated with tBHQ or dtBHQ at 15 µM in the presence or absence of 2 µM Mn2BuOE for 24 hours. Percent viability was determined as for MDA-MB-231 cells, with n=6 (biological replicates).

Unlike tBHQ, dtBHQ has no effect on PC3 prostate cancer cells in combination with Mn2BuOE. These data support the hypothesis that the quinone (see FIGS. 3 and 10) is the toxic agent in PC3 prostate cancer cells, as well as in Jurkat cells. Given that PC3 prostate cancer cells are adherent prostate cancer cells and Jurkats are suspension T-cells, this mechanism appears to be general across cancer cell types.

Referring to FIG. 23, catalase rescues PC3 prostate cells from toxicity of the tBHQ and Mn2BuOE combination treatment. PC3 prostate cancer cells were treated either with vehicle or a combination of 15 µM tBHQ and 2 µM Mn2BuOE in the presence or absence of catalase for 24 h. Percent viability was determined as for MDA-MB-231 cells. Data were normalized to vehicle alone, with n=6 (biological replicates).

Catalase inclusion in cell culture media reduces both extracellular and intracellular levels of hydrogen peroxide. The latter is made possible by the ability of hydrogen peroxide to cross the extracellular membrane both passively as an uncharged molecule and through aquaporin transporters. The inclusion of catalase completely prevented the toxicity of the tBHQ and Mn2BuOE treatment to PC3 prostate cancer cells.

Catalase is an enzyme catalyzing the decomposition of hydrogen peroxide to water and oxygen. These data support the hypothesis that the quinone (see FIGS. 3 and 10) generates hydrogen peroxide, which is also responsible for cell death. The data support a model in which the $H_2O_2$ from oxidation of tBHQ to tBQ is NOT responsible for cell death (based on the dtBHQ result), but $H_2O_2$ generated by the tBQ quinone is responsible for cell death.

In addition to $H_2O_2$ generation, the quinone produced is an electrophile that is toxic to cancer cells. As described above, for example, in FIGS. 4, 11, 12, the experimental data support a mechanism, in which the quinone such as tBQ, formed by oxidation of tBHQ catalyzed by MnTMPyP (FIG. 2), is responsible for death of the cancel cells such as Jurkat cells. Given the generation of mitochondrial superoxide by the treatment, shown in FIG. 9, a likely mechanism of cell death is disruption of the electron transport chain (ETC) by covalent modification of ETC dehydrogenases, leading to generation of superoxide in the mitochondria, causing apoptosis.

Based on the results described above, the oxidizable diphenol and the manganese porphyrin may be used at a molar ratio in a range of from about 1:3 to about 5:1, for example, from about 1:2 to about 5:3.

Comparative experiments were also performed using ascorbic acid other than oxidizable phenols. Oxidation of ascorbic acid may be catalyzed by MnTMPyP. Electrons are donated to oxygen, resulting in the production of hydrogen peroxide ($H_2O_2$). The resulting oxidized form, dehydroascorbate, is recycled by cellular reductases to ascorbic acid, creating a cycle of oxidation and reduction that can result in the accumulation of large amounts of hydrogen peroxide. Cancer cells are much more susceptible to hydrogen peroxide than normal cells.

Figure 24:
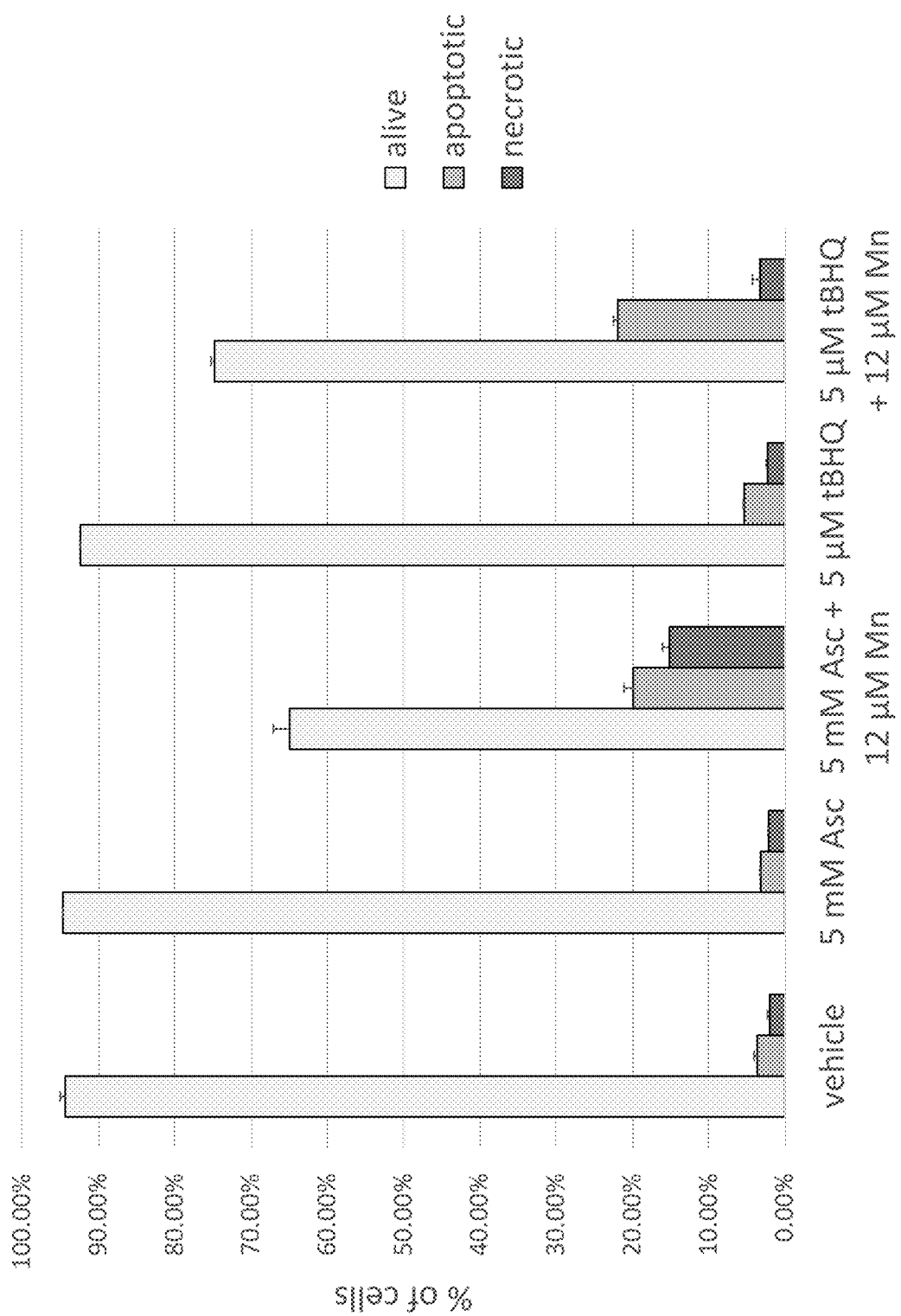
FIG. 24 shows the testing results illustrating that the combination of tBHQ and MnTMPyP is approximately 1,000× more potent than a combination of ascorbic acid and MnTMPyP.

Referring to FIG. 24, the data show that a combination of tBHQ and MnTMPyP is 1000 times more potent than a combination ascorbic acid+MnTMPyP at killing Jurkat leukemia cells (FIG. 24). Jurkat cells were treated with 5 mM ascorbic acid or 5 μM tBHQ with or without 12 μM MnTMPyP for 4 h. Apoptosis was measured using Annexin-PE, necrosis with RedDot 2. Fluorescence was read on an Accuri C6 flow cytometer, with excitation from a 488 nm laser, and FL2 and FL4 filters.

Based on the testing results described above, for examples in FIGS. 6 and 17, the composition described in the present disclosure can kill cancer cells, with no or minimal harm to healthy cells. FIG. 6 compares Jurkat leukemic T cells with primary CD8 cells. CD8 cells are another type of white blood cell, with the role of "killer cell" in the immune response. The results in FIG. 6 shows that the treatment is much more toxic to the leukemic T cells than the primary (e.g. healthy) CD8 cells.

The combination of an oxidizable phenol with a manganese porphyrin is expected to reduce tumor size and other markers of efficacy, either as a stand-alone treatment or offering improved benefits in combination with a chemotherapeutic. The dosage for a pharmaceutically effective amount of an oxidizable diphenol may be any suitable dosage such as in a range of from 0.5 mg/kg to 700 mg/kg, for example, 0.5 mg/kg to 100 mg/kg, 0.5 mg/kg to 20 mg/kg, from 0.5 mg/kg to 10 mg/kg. The dosage for a pharmaceutically effective amount of a manganese porphyrin may be any suitable dosage such as in a range of from 1 mg/kg to 40 mg/kg, for example, from 1 mg/kg to 20 mg/kg.

Although the subject matter has been described in terms of exemplary embodiments, it is not limited thereto. Rather, the appended claims should be construed broadly, to include other variants and embodiments, which may be made by those skilled in the art.

What is claimed is:

1. A pharmaceutical composition for killing cancer cells, comprising a pharmaceutically effective amount of an oxidizable diphenol and a pharmaceutically effective amount of a manganese porphyrin
wherein the oxidizable diphenol is tert-butylhydroquinone (tBHQ).

2. The pharmaceutical composition of claim 1, wherein the manganese porphyrin is manganese (III) substituted pyridyl porphyrin.

3. The pharmaceutical composition of claim 1, wherein the manganese porphyrin is manganese (III) tetrakis (N-alkyl pyridyl) porphyrin, manganese (III) tetrakis (N-alkoxyl pyridyl) porphyrin, or a combination thereof.

4. The pharmaceutical composition of claim 3, wherein the pyridyl is 2-pyridyl, 3-pyridyl, 4-pyridyl, or any combination thereof, and the alkyl or alkoxyl is optionally further substituted.

5. The pharmaceutical composition of claim 1, wherein the manganese porphyrin is selected from manganese (III) tetrakis (N-alkyl 2-pyridyl) porphyrin, manganese (III) tetrakis (N-alkyl 3-pyridyl) porphyrin, manganese (III) tetrakis (N-alkyl 4-pyridyl) porphyrin, manganese (III) tetrakis (N-alkoxyl 2-pyridyl) porphyrin, manganese (III) tetrakis (N-alkoxyl 3-pyridyl) porphyrin, manganese (III) tetrakis (N-alkoxyl 4-pyridyl) porphyrin, and any substituted derivative thereof or any combination thereof.

6. The pharmaceutical composition of claim 1, wherein the manganese porphyrin is manganese (III) tetrakis (N-methyl-4-pyridyl) porphyrin (MnTMPyP), manganese (III) meso-tetrakis (N-ethylpyridinium-2-yl) porphyrin (MnTE-2-PyP), manganese (III) meso-tetrakis (N-n-butoxyethyl-pyridinium-2-yl) porphyrin (MnTNBuOE-2-PyP), or any combination thereof.

7. The pharmaceutical composition of claim 1, wherein the pharmaceutical composition is in one-part dry dosage form, or a two-part dosage form.

8. The pharmaceutical composition of claim 1, wherein the oxidizable diphenol and the manganese porphyrin are at a molar ratio in a range of from 1:3 to 5:1.

9. A method for killing cancer cells in a subject in need thereof, comprising administrating a pharmaceutically effective amount of an oxidizable diphenol and a pharmaceutically effective amount of a manganese porphyrin to the subject so as to kill cancer cells, wherein the oxidizable diphenol is butylhydroquinone (tBHQ).

10. The method of claim 9, wherein the oxidizable diphenol and the manganese porphyrin are simultaneously administrated orally in one dry dosage form.

11. The method of claim 9, wherein the oxidizable diphenol and the manganese porphyrin are orally administrated sequentially in a two-part dosage form.

12. The method of claim 9, wherein the manganese porphyrin is manganese (III) N-substituted pyridyl porphyrin.

13. The method of claim 9, wherein the manganese porphyrin is manganese (III) tetrakis (N-alkyl pyridyl) porphyrin, manganese (III) tetrakis (N-alkoxyl pyridyl) porphyrin, or a combination thereof.

14. The method of claim 13, wherein the pyridyl is 2-pyridyl, 3-pyridyl, 4-pyridyl, or any combination thereof, and the alkyl or alkoxyl is optionally further substituted.

15. The method of claim 9, wherein the manganese porphyrin is selected from manganese (III) tetrakis (N-alkyl 2-pyridyl) porphyrin, manganese (III) tetrakis (N-alkyl 3-pyridyl) porphyrin, manganese (III) tetrakis (N-alkyl 4-pyridyl) porphyrin, manganese (III) tetrakis (N-alkoxyl 2-pyridyl) porphyrin, manganese (III) tetrakis (N-alkoxyl 3-pyridyl) porphyrin, manganese (III) tetrakis (N-alkoxyl 4-pyridyl) porphyrin, and any substituted derivative thereof or any combination thereof.

16. The method of claim 9, wherein the manganese porphyrin is manganese (III) tetrakis (N-methyl-4-pyridyl) porphyrin (MnTMPyP), manganese (III) meso-tetrakis (N-ethylpyridinium-2-yl) porphyrin (MnTE-2-PyP), manganese (III) meso-tetrakis (N-n-butoxyethyl-pyridinium-2-yl) porphyrin (MnTNBuOE-2-PyP), or any combination thereof.

17. The method of claim 9, wherein the oxidizable diphenol and the manganese porphyrin are at a molar ratio in a range of from 1:3 to 5:1.

18. The method of claim 9, wherein the cancer is pancreatic cancer, acute T cell leukemia, acute lymphoblastic leukemia, breast cancer, or prostate cancer.

* * * * *

UNITED STATES PATENT AND TRADEMARK OFFICE
CERTIFICATE OF CORRECTION

PATENT NO. : 12,201,649 B2
APPLICATION NO. : 17/985504
DATED : January 21, 2025
INVENTOR(S) : Aimee Eggler et al.

Page 1 of 1

It is certified that error appears in the above-identified patent and that said Letters Patent is hereby corrected as shown below:

In the Claims

Column 16, Line 56 (Claim 9), insert --tert- -- before "butylhydroquinone (tBHQ)."

Signed and Sealed this
Eighteenth Day of February, 2025

Coke Morgan Stewart
*Acting Director of the United States Patent and Trademark Office*